United States Patent [19]

Olsen et al.

[11] Patent Number: 5,643,783
[45] Date of Patent: Jul. 1, 1997

[54] COLLAGEN AND USES THEREFOR

[75] Inventors: Bjorn R. Olsen, Milton; Suk P. Oh, Chelsea, both of Mass.

[73] Assignee: President and Fellows of Harvard College, Cambridge, Mass.

[21] Appl. No.: 159,784

[22] Filed: Dec. 1, 1993

[51] Int. Cl.$^6$ .............................. C12N 5/00; C12P 21/00; A61K 38/17; C07H 19/00

[52] U.S. Cl. ................. 435/325; 435/69.1; 435/252.3; 435/320.1; 435/365; 530/356; 536/22.1; 536/23.1; 536/23.5

[58] Field of Search ................................. 435/69.1, 252.3, 435/240.2, 320.1; 530/356; 536/22.1, 23.1, 23.5

[56] References Cited

PUBLICATIONS

Gupta et al., "Primary antibody responses to a well-defined and unique hapten are not enhanced by preimmunization with carrier: Analysis in a viral model" PNAS 83:2604–2608, 1986.

Irwin et al., "Use of the Monoclonal antibodies to locate the Chondroitin Sulfate Chain(s) in Type IX collagen" J. Biological Chemistry 261:16281–16283, 1986.

Koch et al., "A major oligomeric fibroblast proteoglycan identified as a novel large form of type–XII collagen", Eur. J. Biochem. 207:847–856, 1992.

Mercurio, "Disruption of oligosaccharide processing in murine tumor cells inhibits their susceptibility to lysis by activated mouse macrophages", PNAS 83:2609–2613, 1986.

Watt et al., "Characterization of collagen types XII and XIV from fetal bovine cartilage", J. Biological Chemistry 267:20093–20099, 1992.

Primary Examiner—Robert A. Wax
Assistant Examiner—Hyosuk Kim
Attorney, Agent, or Firm—Fish & Richardson, P.C.

[57] ABSTRACT

The invention features a novel collagen, type α1 (XVIII) collagen, and uses therefor.

8 Claims, 18 Drawing Sheets

```
GAG AAT GTT GCT GAG GAG GTG GGG CTG CTG CAG CTC CTT GGA GAC CCC
                48
Glu Asn Val Ala Glu Glu Val Gly Leu Leu Gln Leu Leu Gly Asp Pro
1                5                   10                  15

CTA CCT GAG AAG ATC TCA CAA ATC GAT GAC CCT CAC GTC GGG CCG GCC
                96
Leu Pro Glu Lys Ile Ser Gln Ile Asp Asp Pro His Val Gly Pro Ala
            20                  25                  30

TAC ATC TTT GGA CCA GAC TCC AAC AGT GGC CAG GTG GCC CAG TAT CAT
                144
Tyr Ile Phe Gly Pro Asp Ser Asn Ser Gly Gln Val Ala Gln Tyr His
        35                  40                  45

TTC CCA AAA CTC TTC TTC CGG GAC TTT TCG CTG CTG TTT CAT GTC CGG
                192
Phe Pro Lys Leu Phe Phe Arg Asp Phe Ser Leu Leu Phe His Val Arg
    50                  55                  60

CCA GCC ACA GAG GCA GCA GGG GTG CTA TTT GCC ATC ACA GAT GCT GCC
                240
Pro Ala Thr Glu Ala Ala Gly Val Leu Phe Ala Ile Thr Asp Ala Ala
65              70                  75                  80

CAG GTG GTA GTC TCA CTG GGC GTG AAG CTC TCA GAG GTC CGA GAT GGA
                288
Gln Val Val Val Ser Leu Gly Val Lys Leu Ser Glu Val Arg Asp Gly
                85                  90                  95

CAG CAA AAC ATC TCA TTG CTC TAC ACG GAG CCT GGG GCC AGC CAG ACC
                336
Gln Gln Asn Ile Ser Leu Leu Tyr Thr Glu Pro Gly Ala Ser Gln Thr
                100                 105                 110

CAG ACG GGA GCC AGC TTC CGC CTA CCT GCA TTT GTT GGG CAG TGG ACA
                384
Gln Thr Gly Ala Ser Phe Arg Leu Pro Ala Phe Val Gly Gln Trp Thr
            115                 120                 125
```

FIG. 2A

```
CAC TTC GCG CTC AGC GTC GAC GGA GGC TCT GTG GCT CTC TAC GTA GAC
                    432
His Phe Ala Leu Ser Val Asp Gly Gly Ser Val Ala Leu Tyr Val Asp
    130             135             140

TGT GAA GAA TTC CAG AGG GTG CCA TTT GCT CGG GCC TCG CAG GGA CTG
                    480
Cys Glu Glu Phe Gln Arg Val Pro Phe Ala Arg Ala Ser Gln Gly Leu
145             150             155             160

GAG CTA GAG CGT GGC GCT GGC CTC TTT GTG GGT CAG GCT GGA ACA GCA
                    528
Glu Leu Glu Arg Gly Ala Gly Leu Phe Val Gly Gln Ala Gly Thr Ala
                165             170             175

GAC CCT GAC AAG TTC CAG GGG ATG ATC TCA GAG CTG AAG GTA CGC AAA
                    576
Asp Pro Asp Lys Phe Gln Gly Met Ile Ser Glu Leu Lys Val Arg Lys
                180             185             190

ACC CCC CGG GTG AGC CCT GTG CAC TGT CTG GAT GAA GAA GAT GAT GAT
                    624
Thr Pro Arg Val Ser Pro Val His Cys Leu Asp Glu Glu Asp Asp Asp
            195             200             205

GAA GAC CGG GCA TCT GGA GAT TTT GGA AGT GGC TTT GAA GAA AGC AGC
                    672
Glu Asp Arg Ala Ser Gly Asp Phe Gly Ser Gly Phe Glu Glu Ser Ser
        210             215             220

AAG TCA CAC AAG GAG GAT ACA TCT CTA CTA CCT GGG CTC CCT CAG CCA
                    720
Lys Ser His Lys Glu Asp Thr Ser Leu Leu Pro Gly Leu Pro Gln Pro
225             230             235             240

CCT CCT GTC ACT TCC CCA CCC CTG GCT GGA GGC AGC ACC ACA GAA GAT
                    768
Pro Pro Val Thr Ser Pro Pro Leu Ala Gly Gly Ser Thr Thr Glu Asp
                245             250             255

CCT AGA ACA GAA GAA ACG GAG GAA GAC GCC GCG GTA GAT TCT ATA GGA
                    816
Pro Arg Thr Glu Glu Thr Glu Glu Asp Ala Ala Val Asp Ser Ile Gly
            260             265             270

GCT GAG ACC CTT CCT GGC ACA GGT TCA AGC GGT GCA TGG GAT GAG GCT
                    864
Ala Glu Thr Leu Pro Gly Thr Gly Ser Ser Gly Ala Trp Asp Glu Ala
        275             280             285

ATC CAG AAC CCC GGA AGG GGC TTG ATA AAG GGA GGT ATG AAA GGA CAA
                    912
Ile Gln Asn Pro Gly Arg Gly Leu Ile Lys Gly Gly Met Lys Gly Gln
290             295             300
```

FIG. 2B

```
AAG GGA GAA CCA GGT GCC CAG GGC CCA CCT GGC CCA GCT GGC CCC CAG
                                960
Lys Gly Glu Pro Gly Ala Gln Gly Pro Pro Gly Pro Ala Gly Pro Gln
305             310             315             320

GGT CCT GCC GGT CCA GTG GTC CAG AGC CCC AAC TCA CAA CCT GTC CCT
                               1008
Gly Pro Ala Gly Pro Val Val Gln Ser Pro Asn Ser Gln Pro Val Pro
                325             330             335

GGA GCA CAA GGA CCC CCG GGA CCT CAG GGG CCA CCA GGG AAG GAT GGC
                               1056
Gly Ala Gln Gly Pro Pro Gly Pro Gln Gly Pro Pro Gly Lys Asp Gly
            340             345             350

ACT CCA GGA AGG GAT GGT GAA CCG GGT GAC CCT GGT GAA GAT GGG AGA
                               1104
Thr Pro Gly Arg Asp Gly Glu Pro Gly Asp Pro Gly Glu Asp Gly Arg
            355             360             365

CCG GGT GAC ACT GGA CCT CAA GGC TTT CCA GGG ACC CCA GGA GAT GTG
                               1152
Pro Gly Asp Thr Gly Pro Gln Gly Phe Pro Gly Thr Pro Gly Asp Val
        370             375             380

GGC CCT AAG GGC GAG AAG GGA GAT CCT GGT ATT GGG CCC CGA GGA CCT
                               1200
Gly Pro Lys Gly Glu Lys Gly Asp Pro Gly Ile Gly Pro Arg Gly Pro
385             390             395             400

CCA GGG CCT CCA GGG CCA CCA GGA CCC TCC TTC AGA CAA GAC AAG CTG
                               1248
Pro Gly Pro Pro Gly Pro Pro Gly Pro Ser Phe Arg Gln Asp Lys Leu
            405             410             415

ACC TTC ATT GAC ATG GAG GGA TCC GGT TTC AGC GGA GAC ATA GAG AGC
                               1296
Thr Phe Ile Asp Met Glu Gly Ser Gly Phe Ser Gly Asp Ile Glu Ser
            420             425             430

CTT AGA GGC CCA CGA GGC TTC CCT GGC CCC CCG GGG CCC CCT GGT GTC
                               1344
Leu Arg Gly Pro Arg Gly Phe Pro Gly Pro Pro Gly Pro Pro Gly Val
            435             440             445

CCA GGA CTT CCT GGT GAG CCA GGA CGC TTT GGG ATC AAT GGT TCC TAT
                               1392
Pro Gly Leu Pro Gly Glu Pro Gly Arg Phe Gly Ile Asn Gly Ser Tyr
        450             455             460

GCA CCA GGA CCT GCA GGC CTT CCT GGT GTA CCT GGG AAG GAA GGA CCC
                               1440
Ala Pro Gly Pro Ala Gly Leu Pro Gly Val Pro Gly Lys Glu Gly Pro
465             470             475             480
```

FIG. 2C

```
CCC GGT TTT CCA GGT CCC CCG GGA CCT CCA GGT CCT CCA GGC AAA GAG
            1488
Pro Gly Phe Pro Gly Pro Pro Gly Pro Pro Gly Pro Pro Gly Lys Glu
                485             490             495

GGC CCA CCA GGA GTG GCC GGC CAG AAA GGC AGT GTT GGT GAT GTG GGC
            1536
Gly Pro Pro Gly Val Ala Gly Gln Lys Gly Ser Val Gly Asp Val Gly
                500             505             510

ATC CCA GGA CCC AAG GGG AGC AAA GGA GAC CTT GGG CCC ATC GGT ATG
            1584
Ile Pro Gly Pro Lys Gly Ser Lys Gly Asp Leu Gly Pro Ile Gly Met
                515             520             525

CCT GGC AAG TCT GGC TTG GCT GGA TCC CCT GGG CCA GTT GGA CCC CCA
            1632
Pro Gly Lys Ser Gly Leu Ala Gly Ser Pro Gly Pro Val Gly Pro Pro
                530             535             540

GGA CCT CCA GGG CCT CCA GGG CCA CCA GGA CCA GGA TTT GCT GCT GGA
            1680
Gly Pro Pro Gly Pro Pro Gly Pro Pro Gly Pro Gly Phe Ala Ala Gly
545             550             555             560

TTC GAT GAT ATG GAA GGC TCT GGA ATA CCC CTC TGG ACA ACA GCC CGA
            1728
Phe Asp Asp Met Glu Gly Ser Gly Ile Pro Leu Trp Thr Thr Ala Arg
                565             570             575

AGC TCT GAT GGG CTG CAG GGA CCT CCC GGG TCG CCG GGA CTC AAG GGG
            1776
Ser Ser Asp Gly Leu Gln Gly Pro Pro Gly Ser Pro Gly Leu Lys Gly
                580             585             590

GAT CCT GGA GTG GCA GGC CTA CCT GGA GCC AAG GGA GAA GTT GGA GCA
            1824
Asp Pro Gly Val Ala Gly Leu Pro Gly Ala Lys Gly Glu Val Gly Ala
                595             600             605

GAT GGA GCC CAG GGC ATC CCT GGT CCC CCA GGA AGA GAA GGT GCA GCT
            1872
Asp Gly Ala Gln Gly Ile Pro Gly Pro Pro Gly Arg Glu Gly Ala Ala
                610             615             620

GGA TCT CCG GGG CCA AAA GGA GAG AAG GGG ATG CCG GGA GAA AAG GGA
            1920
Gly Ser Pro Gly Pro Lys Gly Glu Lys Gly Met Pro Gly Glu Lys Gly
625             630             635             640

AAC CCA GGA AAA GAT GGA GTG GGC CGG CCG GGC CTC CCT GGG CCT CCA
            1968
Asn Pro Gly Lys Asp Gly Val Gly Arg Pro Gly Leu Pro Gly Pro Pro
                645             650             655
```

FIG. 2D

```
GGA CCT CCA GGG CCT GTG ATC TAT GTG TCA AGT GAG GAT AAA GCA ATA
            2016
Gly Pro Pro Gly Pro Val Ile Tyr Val Ser Ser Glu Asp Lys Ala Ile
        660             665             670

GTG AGC ACG CCA GGA CCT GAG GGC AAG CCA GGG TAC GCA GGC TTT CCT
            2064
Val Ser Thr Pro Gly Pro Glu Gly Lys Pro Gly Tyr Ala Gly Phe Pro
        675             680             685

GGA CCT GCT GGA CCG AAG GGT GAC CTG GGT TCC AAA GGC GAG CAG GGT
            2112
Gly Pro Ala Gly Pro Lys Gly Asp Leu Gly Ser Lys Gly Glu Gln Gly
        690             695             700

CTT CCG GGG CCC AAG GGT GAG AAG GGA GAG CCA GGC ACT ATC TTT AGT
            2160
Leu Pro Gly Pro Lys Gly Glu Lys Gly Glu Pro Gly Thr Ile Phe Ser
705             710             715             720

CCT GAT GGC AGA GCT CTG GGC CAT CCC CAG AAG GGA GCC AAG GGA GAG
            2208
Pro Asp Gly Arg Ala Leu Gly His Pro Gln Lys Gly Ala Lys Gly Glu
        725             730             735

CCA GGC TTT CGA GGA CCC CCG GGT CCT TAT GGA CGA CCT GGG CAC AAG
            2256
Pro Gly Phe Arg Gly Pro Pro Gly Pro Tyr Gly Arg Pro Gly His Lys
        740             745             750

GGT GAA ATT GGC TTC CCT GGA CGG CCG GGT CGA CCT GGA ACG AAT GGC
            2304
Gly Glu Ile Gly Phe Pro Gly Arg Pro Gly Arg Pro Gly Thr Asn Gly
        755             760             765

TTA AAG GGA GAG AAG GGA GAG CCT GGA GAT GCC AGC CTT GGG TTC AGC
            2352
Leu Lys Gly Glu Lys Gly Glu Pro Gly Asp Ala Ser Leu Gly Phe Ser
770             775             780

ATG AGG GGA TTG CCT GGC CCC CCT GGG CCT CCA GGA CCC CCA GGT CCT
            2400
Met Arg Gly Leu Pro Gly Pro Pro Gly Pro Pro Gly Pro Pro Gly Pro
785             790             795             800

CCT GGG ATG CCC ATC TAT GAC AGC AAT GCA TTT GTG GAG TCT GGC CGA
            2448
Pro Gly Met Pro Ile Tyr Asp Ser Asn Ala Phe Val Glu Ser Gly Arg
        805             810             815

CCT GGA CTA CCA GGA CAG CAG GGT GTG CAG GGG CCT TCA GGA CCA AAG
            2496
Pro Gly Leu Pro Gly Gln Gln Gly Val Gln Gly Pro Ser Gly Pro Lys
        820             825             830
```

FIG. 2E

```
GGT GAC AAA GGA GAG GTG GGC CCA CCT GGG CCA CCA GGG CAA TTC CCC
            2544
Gly Asp Lys Gly Glu Val Gly Pro Pro Gly Pro Pro Gly Gln Phe Pro
        835             840             845

ATT GAC CTC TTC CAC CTG GAA GCG GAA ATG AAG GGG GAC AAG GGA GAC
            2592
Ile Asp Leu Phe His Leu Glu Ala Glu Met Lys Gly Asp Lys Gly Asp
    850             855             860

CGA GGG GAT GCT GGA CAG AAA GGA GAG AGG GGA GAA CCT GGG GCT CCT
            2640
Arg Gly Asp Ala Gly Gln Lys Gly Glu Arg Gly Glu Pro Gly Ala Pro
865             870             875             880

GGT GGT GGA TTC TTC AGC TCA AGT GTA CCT GGC CCA CCC GGC CCA CCT
            2688
Gly Gly Gly Phe Phe Ser Ser Ser Val Pro Gly Pro Pro Gly Pro Pro
                885             890             895

GGA TAC CCT GGA ATT CCG GGT CCA AAG GGA GAG AGC ATC CGG GGG CCA
            2736
Gly Tyr Pro Gly Ile Pro Gly Pro Lys Gly Glu Ser Ile Arg Gly Pro
            900             905             910

CCT GGC CCT CCT GGC CCG CAG GGA CCT CCT GGC ATT GGC TAT GAG GGT
            2784
Pro Gly Pro Pro Gly Pro Gln Gly Pro Pro Gly Ile Gly Tyr Glu Gly
            915             920             925

CGC CAG GGT CCC CCA GGA CCT CCA GGA CCT CCA GGA CCT CCC TCC TTC
            2832
Arg Gln Gly Pro Pro Gly Pro Pro Gly Pro Pro Gly Pro Pro Ser Phe
    930             935             940

CCT GGC CCT CAC AGA CAG ACT GTC AGT GTT CCT GGT CCT CCG GGC CCA
            2880
Pro Gly Pro His Arg Gln Thr Val Ser Val Pro Gly Pro Pro Gly Pro
945             950             955             960

CCT GGT CCT CCA GGT CCC CCA GGA GCC ATG GGT GCC TCT GCT GGG CAG
            2928
Pro Gly Pro Pro Gly Pro Pro Gly Ala Met Gly Ala Ser Ala Gly Gln
            965             970             975

GTG AGG ATC TGG GCC ACA TAC CAG ACC ATG CTG GAC AAG ATC CGG GAG
            2976
Val Arg Ile Trp Ala Thr Tyr Gln Thr Met Leu Asp Lys Ile Arg Glu
        980             985             990

GTG CCG GAG GGC TGG CTC ATC TTT GTG GCC GAG AGG GAA GAG CTC TAT
            3024
Val Pro Glu Gly Trp Leu Ile Phe Val Ala Glu Arg Glu Glu Leu Tyr
```

GTA CGC GTT AGA AAT GGC TTC CGG AAG GTG CTG CTG GAG GCC CGG ACA
                    3072
    Val Arg Val Arg Asn Gly Phe Arg Lys Val Leu Leu Glu Ala Arg Thr
       1010                1015                1020

GCC CTC CTG AGA GGC ACG GGC AAT GAG GTG GCT GCT TTC CAG CCC CCA
                    3120
    Ala Leu Leu Arg Gly Thr Gly Asn Glu Val Ala Ala Phe Gln Pro Pro
   1025                1030                1035                1040

TTG GTC CAG CTT CAT GAG GGC AGT CCA TAC ACC CGG AGG GAG TAC TCC
                    3168
    Leu Val Gln Leu His Glu Gly Ser Pro Tyr Thr Arg Arg Glu Tyr Ser
                   1045                1050                1055

TAT TCC ACG GCA CGA CCC TGG CGA GCA GAT GAC ATC CTG GCC AAC CCA
                    3216
    Tyr Ser Thr Ala Arg Pro Trp Arg Ala Asp Asp Ile Leu Ala Asn Pro
               1060                1065                1070

CCG CGC CTG CCA GAC CGC CAG CCT TAC CCT GGA GTT CCA CAT CAC CAC
                    3264
    Pro Arg Leu Pro Asp Arg Gln Pro Tyr Pro Gly Val Pro His His His
               1075                1080                1085

AGT TCC TAT GTG CAC CTG CCG CCA GCC CGC CCC ACC CTC TCA CTT GCT
                    3312
    Ser Ser Tyr Val His Leu Pro Pro Ala Arg Pro Thr Leu Ser Leu Ala
               1090                1095                1100

CAT ACT CAT CAG GAC TTT CAG CCA GTG CTC CAC CTG GTG GCA CTG AAC
                    3360
    His Thr His Gln Asp Phe Gln Pro Val Leu His Leu Val Ala Leu Asn
   1105                1110                1115                1120

ACC CCC CTG TCT GGA GGC ATG CGT GGT ATC CGT GGA GCA GAT TTC CAG
                    3408
    Thr Pro Leu Ser Gly Gly Met Arg Gly Ile Arg Gly Ala Asp Phe Gln
                   1125                1130                1135

TGC TTC CAG CAA GCC CGA GCC GTG GGG CTG TCG GGC ACC TTC CGG GCT
                    3456
    Cys Phe Gln Gln Ala Arg Ala Val Gly Leu Ser Gly Thr Phe Arg Ala
               1140                1145                1150
```

FIG. 2G

```
TTC CTG TCC TCT AGG CTG CAG GAT CTC TAT AGC ATC GTG CGC CGT GCT
            3504
Phe Leu Ser Ser Arg Leu Gln Asp Leu Tyr Ser Ile Val Arg Arg Ala
        1155                1160                1165

GAC CGG GGG TCT GTG CCC ATC GTC AAC CTG AAG GAC GAG GTG CTA TCT
            3552
Asp Arg Gly Ser Val Pro Ile Val Asn Leu Lys Asp Glu Val Leu Ser
        1170                1175                1180

CCC AGC TGG GAC TCC CTG TTT TCT GGC TCC CAG GGT CAA GTG CAA CCC
            3600
Pro Ser Trp Asp Ser Leu Phe Ser Gly Ser Gln Gly Gln Val Gln Pro
1185                1190                1195                1200

GGG GCC CGC ATC TTT TCT TTT GAC GGC AGA GAT GTC CTG AGA CAC CCA
            3648
Gly Ala Arg Ile Phe Ser Phe Asp Gly Arg Asp Val Leu Arg His Pro
                1205                1210                1215

GCC TGG CCG CAG AAG AGC GTA TGG CAC GGC TCG GAC CCC AGT GGG CGG
            3696
Ala Trp Pro Gln Lys Ser Val Trp His Gly Ser Asp Pro Ser Gly Arg
        1220                1225                1230

AGG CTG ATG GAG AGT TAC TGT GAG ACA TGG CGA ACT GAA ACT ACT GGG
            3744
Arg Leu Met Glu Ser Tyr Cys Glu Thr Trp Arg Thr Glu Thr Thr Gly
        1235                1240                1245

GCT ACA GGT CAG GCC TCC TCC CTG CTG TCA GGC AGG CTC CTG GAA CAG
            3792
Ala Thr Gly Gln Ala Ser Ser Leu Leu Ser Gly Arg Leu Leu Glu Gln
        1250                1255                1260

AAA GCT GCG AGC TGC CAC AAC AGC TAC ATC GTC CTG TGC ATT GAG AAT
            3840
Lys Ala Ala Ser Cys His Asn Ser Tyr Ile Val Leu Cys Ile Glu Asn
1265                1270                1275                1280

AGC TTC ATG ACC TCT TTC TCC AAA TAGGCCTCTG CCAGCTAGGG
            3884
Ser Phe Met Thr Ser Phe Ser Lys
                1285

TGGCAGACAG AGGCCATGCA GAACTTTGAC ACAGCGCAGG GAGCATTCAG TCAGCACCCA
            3944

GGGCTCTGGC TGGGATACAA CTCCTGTATA GTTCCCATTT TTATGTAATC CTCAAGAAAT
        4004

AAAAGGAAGC CAAAGAGTAA AAAAAAA   (SEQ ID NO: 1)
        4031
```

FIG. 2H

α1(XVIII)  LPPARPTLSLAHTHQDFQPVLHLVALNTPLSGGMRGIRGADFQCFQQARAVGLSGTFRAF (SEQ ID NO:2)
             |*|||*|||  |  ||*||   |      |||||*|| |||
α1(XV)     PHQLLPPPNPISSANYEKPALHLAALNMPFSGDIR----ADFQCFKQARAAGLLSTYYRAP (SEQ ID NO:3)

α1(XVIII)  LSSRLQDLYSIVRRADRGSVPIVNLKDEVLSPSWDSLFSGSGQVQPGARIFSFDGRDVL
           ||| ||||  |||*|  |||||||||  ||  ||  ||*  |||||||*
α1(XV)     LSSHLQDLSTIVRKAERYSLPIVNLKGQVLFNNWDSIPSGHGGQPRMHIPIYSFDGRDIM

α1(XVIII)  RHPAWPQKSVWHGSDPSGRRLMESYCETWRTETTGATGQASSLLSGRLLEQKAASCHNSY
           |  || *|||  ||  ||   |  |||    ||*|||**|||*||  |
α1(XV)     TDPSWPQKVIWHGSSPHGVRLVDNYCEAWRTADTAVTGLASPLSTGKILDQKAYSCANRL

α1(XVIII)  IVLCIENSFMTSFSK&
           |||||||||||  |  |
α1(XV)     IVLCIENSFMTDARK&

FIG. 4

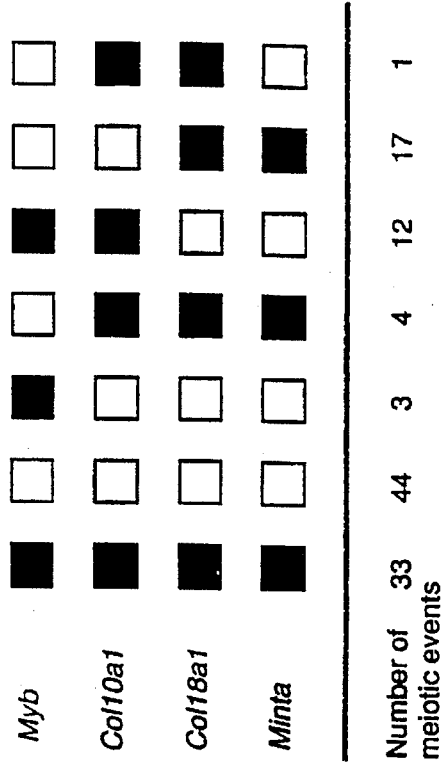

FIG. 8

```
GGA GAA GTT GGA GCA GAT GGA ATC CCC GGG TTC CCC GGC CTC CCT GGC
            48
Gly Glu Val Gly Ala Asp Gly Ile Pro Gly Phe Pro Gly Leu Pro Gly
1           5               10              15

AGA GAG GGC ATT GCT GGG CCC CAG GGG CCA AAG GGA GAC AGA GGC AGC
            96
Arg Glu Gly Ile Ala Gly Pro Gln Gly Pro Lys Gly Asp Arg Gly Ser
            20              25              30

CGG GGA GAA AAG GGA GAT CCA GGG AAG GAC GGA CTC GGG CAG CCG GGC
            144
Arg Gly Glu Lys Gly Asp Pro Gly Lys Asp Gly Leu Gly Gln Pro Gly
            35              40              45

CTC CCT GGC CCC CGC GGA CCC CCG GGA CCT GTG GTC TAC GTG TCG GAG
            192
Leu Pro Gly Pro Arg Gly Pro Pro Gly Pro Val Val Tyr Val Ser Glu
    50              55              60

CAG GAC GGA TCC GTC CTG AGC GTG CCG GGA CCT GAG GGC CGG CGG GGT
            240
Gln Asp Gly Ser Val Leu Ser Val Pro Gly Pro Glu Gly Arg Arg Gly
65              70              75              80

TTC GCA GGC TTT CCC GGA CCT GCA GGA CCC AAG GGC AAC CTG GGC TCT
            288
Phe Ala Gly Phe Pro Gly Pro Ala Gly Pro Lys Gly Asn Leu Gly Ser
                85              90              95

AAG GGC GAA CTA GGC TCC CCG GGA CCC AAG GGT GAG AAG GGT GAA CCG
            336
Lys Gly Glu Leu Gly Ser Pro Gly Pro Lys Gly Glu Lys Gly Glu Pro
            100             105             110

GGC AGC ATC TTC AGC CCC GAC GGC GGT GCC CTG GGC CCT GCC CAG AAA
            384
```

FIG. 6A

```
Gly Ser Ile Phe Ser Pro Asp Gly Gly Ala Leu Gly Pro Ala Gln Lys
        115                 120                 125

GGA GCC AAG GGA GAG CCG GGC TTC CGA GGA CCC CCG GGC CTA TAC GGA
                    432
Gly Ala Lys Gly Glu Pro Gly Phe Arg Gly Pro Pro Gly Leu Tyr Gly
        130                 135                 140

CGG CCG GGG TAC AAG GGA GAG ATT GGC TTT CCT GGA CGG CCG GGT CGC
                    480
Arg Pro Gly Tyr Lys Gly Glu Ile Gly Phe Pro Gly Arg Pro Gly Arg
145             150                 155                 160

CCC GGG ATG AAC GGA TTG AAA GGA GAG AAA GGG GAG CCG GGA GAT GCC
                528
Pro Gly Met Asn Gly Leu Lys Gly Glu Lys Gly Glu Pro Gly Asp Ala
                165                 170                 175

AGC CTT GGA TTT GGC ATG AGG GGA ATG CCC GGC CCC CCA GGA CCT CCA
                576
Ser Leu Gly Phe Gly Met Arg Gly Met Pro Gly Pro Pro Gly Pro Pro
            180                 185                 190

GGG CCC CCA GGC CCT CCA GGG ACT CCT GTT TAC GAC AGC AAT GTG TTT
                624
Gly Pro Pro Gly Pro Pro Gly Thr Pro Val Tyr Asp Ser Asn Val Phe
        195                 200                 205

GCT GAG TCC AGC CGC CCC GGG CCT CCA GGA TTG CCA GGG AAT CAG GGC
                672
Ala Glu Ser Ser Arg Pro Gly Pro Pro Gly Leu Pro Gly Asn Gln Gly
    210                 215                 220

CCT CCA GGA CCC AAG GGC CCC AAA GGA GAA GTG GGC CCC CCG GAC CCA
                720
Pro Pro Gly Pro Lys Gly Pro Lys Gly Glu Val Gly Pro Pro Gly Pro
225             230                 235                 240

CCA GGG CAG TTT CCG TTT GAC TTT CTT CAG AAG GAG GCT GAA ATG AAG
                768
Pro Gly Gln Phe Pro Phe Asp Phe Leu Gln Lys Glu Ala Glu Met Lys
        245                 250                 255

GGG GAG AAG GGA GAC CGA GGT GAT GCA GGA CAG AAA GGC GAA AGG GGG
                816
Gly Glu Lys Gly Asp Arg Gly Asp Ala Gly Gln Lys Gly Glu Arg Gly
        260                 265                 270

GAG CCC GGG GGC GGC GGT TTC TTC GGC TCC AGC CTG CCC GGG GCC CCC
                864
Glu Pro Gly Gly Gly Gly Phe Phe Gly Ser Ser Leu Pro Gly Ala Pro
    275                 280                 285
```

FIG. 6B

```
GGC GCC CCA GGC CCA CGT GGC TAC CCT GGG ATT CCA GGT CCC AAG GGA
                912
Gly Ala Pro Gly Pro Arg Gly Tyr Pro Gly Ile Pro Gly Pro Lys Gly
    290             295             300

GAG AGC ATC CGG GGC CAG CCC GGC CCA CCT GGA CCT CAG GGA CCC CCC
                960
Glu Ser Ile Arg Gly Gln Pro Gly Pro Pro Gly Pro Gln Gly Pro Pro
305             310             315                 320

GGC ATC GGC TAC GAG GGG CGC CAG GGC CCT CCC GGC CCC CCA GGC CCC
                1008
Gly Ile Gly Tyr Glu Gly Arg Gln Gly Pro Pro Gly Pro Pro Gly Pro
                325             330                 335

CCA GGG CCC CCT TCA TTT CCT GGC CCT CAC AGG CAG ACT ATC AGC GTT
                1056
Pro Gly Pro Pro Ser Phe Pro Gly Pro His Arg Gln Thr Ile Ser Val
        340             345             350

CCG GGG CCT CCG GGC CCC CCT GGG CCC CCT GGG CCC CCT GGA ACC ATG
                1104
Pro Gly Pro Pro Gly Pro Pro Gly Pro Pro Gly Pro Pro Gly Thr Met
        355             360             365

GGC GCC TCC TCA GGG CAG GTG AGG CTC TGG GCT ACA CGC CAG GCC ATG
                1152
Gly Ala Ser Ser Gly Gln Val Arg Leu Trp Ala Thr Arg Gln Ala Met
        370             375             380

CTG GGC CAG GTG CAC GAG GTT CCC GAG GGC TGG CTC ATC TTC GTG GCC
                1200
Leu Gly Gln Val His Glu Val Pro Glu Gly Trp Leu Ile Phe Val Ala
385             390             395                 400

GAG CAG GAG GAG CTC TAC GTC CGC GTG CAG AAC GGG TTC CGG AAG GTC
                1248
Glu Gln Glu Glu Leu Tyr Val Arg Val Gln Asn Gly Phe Arg Lys Val
            405             410             415

CAG CTG GAG GCC CGG ACA CCA CTC CCA CGA GGG ACG GAC AAT GAA GTG
                1296
Gln Leu Glu Ala Arg Thr Pro Leu Pro Arg Gly Thr Asp Asn Glu Val
        420             425             430

GCC GCC TTG CAG CCC CCC GTG GTG CAG CTG CAC GAC AGC AAC CCC TAC
                1344
Ala Ala Leu Gln Pro Pro Val Val Gln Leu His Asp Ser Asn Pro Tyr
        435             440             445

CCG CGG CGG GAG CAC CCC CAC CCC ACC GCG CGG CCC TGG CGG GCA GAT
                1392
Pro Arg Arg Glu His Pro His Pro Thr Ala Arg Pro Trp Arg Ala Asp
    450             455             460
```

FIG. 6C

```
GAC ATC CTG GCC AGC CCC CCT GGG CTG CCC GAG CCC CAG CCC TAC CCC
            1440
Asp Ile Leu Ala Ser Pro Pro Gly Leu Pro Glu Pro Gln Pro Tyr Pro
465                 470             475                 480

GGA GGC CCG CAC CAC AGC TCC TAC GTG CAC TGC GGC CCG GCA CGA CCC
            1488
Gly Gly Pro His His Ser Ser Tyr Val His Cys Gly Pro Ala Arg Pro
                485             490                 495

ACA AGC CCA CCC GCC CAC AGC CAC CGC GAC TTC CAG CCG GTG CTC CAC
            1536
Thr Ser Pro Pro Ala His Ser His Arg Asp Phe Gln Pro Val Leu His
            500             505                 510

CTG GTT GCG CTC AAC AGC CCC CTG TCA GGC GGC ATG CGG GGC ATC CGC
            1584
Leu Val Ala Leu Asn Ser Pro Leu Ser Gly Gly Met Arg Gly Ile Arg
            515             520             525

GGG GCC GAC TTC CAG TGC TTC CAG CAG GCG CGG GCC GTG GGG CTG GCG
            1632
Gly Ala Asp Phe Gln Cys Phe Gln Gln Ala Arg Ala Val Gly Leu Ala
530             535             540

GGC ACC TTC CGC GCC TTC CTG TCC TCG CGC CTG CAG GAC CTG TAC AGC
            1680
Gly Thr Phe Arg Ala Phe Leu Ser Ser Arg Leu Gln Asp Leu Tyr Ser
545             550             555             560

ATC GTG CGC CGT GCC GAC CGC GCA GCC GTG CCC ATC GTC AAC CTC AAG
            1728
Ile Val Arg Arg Ala Asp Arg Ala Ala Val Pro Ile Val Asn Leu Lys
                565             570             575

GAC GAG CTG CTG TTT CCC AGC TGG GAG GCT CTG TTC TCA GGC TCT GAG
            1776
Asp Glu Leu Leu Phe Pro Ser Trp Glu Ala Leu Phe Ser Gly Ser Glu
            580             585             590

GGT CCG CTG AAG CCC GGG GCA CGC ATC TTC TCC TTT GAC GGC AAG GAC
            1824
Gly Pro Leu Lys Pro Gly Ala Arg Ile Phe Ser Phe Asp Gly Lys Asp
            595             600             605

GTC CTG AGG CAC CCC ACC TGG CCC CAG AAG AGC GTG TGG CAT GGC TCG
            1872
Val Leu Arg His Pro Thr Trp Pro Gln Lys Ser Val Trp His Gly Ser
            610             615             620

GAC CCC AAC GGG CGC AGG CTG ACC GAG AGC TAC TGT GAG ACG TGG CGG
            1920
Asp Pro Asn Gly Arg Arg Leu Thr Glu Ser Tyr Cys Glu Thr Trp Arg
```

FIG. 6D

```
      625                630                635                640
ACG GAG GCT CCC TCG GCC ACG GGC CAG GCC TCC TCG CTG CTG GGG GGC
                1968
Thr Glu Ala Pro Ser Ala Thr Gly Gln Ala Ser Ser Leu Leu Gly Gly
                645                650                655

AGG CTC CTG GGG CAG AGT GCC GCG AGC TGC CAT CAC GCC TAC ATC GTG
                2016
Arg Leu Leu Gly Gln Ser Ala Ala Ser Cys His His Ala Tyr Ile Val
                660                665                670

CTC TGC ATT GAG AAC AGC TTC ATG ACT GCC TCC AAG
                2052
Leu Cys Ile Glu Asn Ser Phe Met Thr Ala Ser Lys
                675                680

TAGCCACCGC CTGGATGCAG ATGGCCGGAG AGGACCGGCG GCTCGGAGGA AGCCCCCACC
                                    2112

GTGGGCAGGG AGCAGCCGGC CAGCCCCTGG CCCCAGGACC TGGCTGCCAT ACTTTCCTGT
                                    2172

ATAGTTCACG TTTCATGTAA TCCTCAAGAA ATAAAAGGAA GCCAAAGAGT GTATTTTTTT
                                    2232

AAAAGTTTAA AACAGAAGCC TGATGCTGAC ATTCACCTGC CCCAACTCTC CCCTGACCTG
                                    2292

TGAGCCCAGC TGGGTCAGGC AGGGTGCAGT ATCATGCCCT GTGCAACCTC TTGGCCTGAT
                                    2352

CAGACCACGG CTCGATTTCT CCAGGATTTC CTGCTTTGGG AAACCGTGCT CGCCCCAGCA
                                    2412

GGTGCTGACT TCATCTCCCA CCTAGCAGCA CCGTTCTGTG CACAAAACCC AGACCTGTTA
                                    2472

GCAGACAGGC CCCGTGAGGC AATGGGAGCT GAGGCCACAC TCAGCACAAG GCCATCTGGG
                                    2532

CTCCTCCAGG GTGTGTGCTC GCCCTGCGGT AGATGGGAGG GAGGCTCAGG TCCCTGGGGC
                                    2592

TAGGGGAGC CCCTTCTGCT CAGCTCTGGG CCATTCTCCA CAGCAACCCC AGGCTGAAGC
                                    2652

AGGTTCCCAA GCTCAGAGGC GCACTGTGAC CCCCAGCTCC GGCCTGTCCT CCAACACCAA
                                    2712

GCACAGCAGC CTGGGGCTGG CCTCCCAAAT GAGCCATGAG ATGATACATC CAAAGCAGAC
                                    2772
```

FIG. 6E

```
AGCTCCACCC TGGCCGAGTC CAAGCTGGGA GATTCAAGGG ACCCATGAGT TGGGGTCTGG
           2832

CAGCCTCCCA TCCAGGGCCC CCATCTCATG CCCCTGGCTG GGACGTGCTC AGCCAGCACT
           2892

TGTCCAGCTG AGCGCCAGGA TGGAACACGG CCACATCAAA GAGGCTGAGG CTGGCACAGG
           2952

ACATGCGGTA GCCAGCACAC AGGGCAGTGA GGGAGGGCTG TCATCTGTGC ACTGCCCATG
           3012

GACAGGCTGG CTCCAGATGC AGGGCAGTCA TTGGCTGTCT CCTAGGAAAC CCATATCCTT
           3072

ACCCTCCTTG GGACTGAAGG GGAACCCCGG GGTGCCCACA GGCCGCCCTG CGGGTGAACA
           3132

AAGCAGCCAC GAGGTGCAAC AAGGTCCTCT GTCAGTCACA GCCACCCCTG AGATCCGGCA
           3192

ACATCAACCC CAGAGTCATT CGTTCTGTGG AGGGACAAGT GGACTCAGGG CAGCGCCAGG
           3252

CTGACCACAG CACAGCCAAC ACGCACCTGC CTCAGGACTG CGACGAAACC GGTGGGGCTG
           3312

GTTCTGTAAT TGTGTGTGAT GTGAAGCCAA TTCAGACAGG CAAATAAAAG TGACCTTTTA
           3372

CACTGAAAAA AAAAAAAAAA AA    (SEQ ID NO: 4)
           3394
```

FIG. 6F

COLLAGEN AND USES THEREFOR

BACKGROUND OF THE INVENTION

The field of the invention is collagen proteins. The structure of extracellular matrices is to a large extent determined by the interaction between collagenous proteins and proteoglycans. Collagenous proteins form the major class of insoluble fibrous protein in the extracellular matrix. Proteoglycans are complex macromolecules found in the extracellular matrix, connective tissue, and on the surface of many cells. Proteoglycans are composed of a core protein to which is attached one or more polysaccharides known as glycosaminoglycans. Within the extracellular matrix collagen molecules participate in the formation of a polymer framework of high tensile strength, while the proteoglycans, because they are hydrophilic and highly anionic, impart resilience.

Collagen polypeptides contain one or more blocks of Gly-x-y repeats, in which y frequently represents prolyl or hydroxyprolyl residues. The presence of such sequence repeats allows groups of three collagen polypeptides to fold into triple-helical domains which are rigid and inextensible.

Within the superfamily of collagens, the fibrillar collagens represents a distinct family (which includes type-I, type-II, type-III, type-V, and type-XI collagen). The triple-helical domains of the proteins polymerize in a staggered fashion to form fibrils.

Members of other collagen families do not by themselves form cross-striated fibrils, but may be associated with fibrils (FACIT or fibril-associated collagens) or form their own distinct polymers (networks in the case of basement membrane collagens or anchoring fibrils in the case of collagen VII). The lengths as well as the number of triple-helical domains within molecules of non-fibrillar collagens are frequently quite different from these domains in fibrillar collagens.

The non-triple-helical domains that separate triple-helical domains in some non-fibrillar collagens represent regions of flexibility. For example, in types IX, XII and XIV collagen non-triple-helical regions form hinges which allow the triple-helical domains on either side to be oriented in a variety of directions. One function on non-triple-helical domains in such collagen types may be to provide for flexibility between rigid triple-helical regions.

SUMMARY OF THE INVENTION

The invention features a novel collagen, type $\alpha 1$ (XVIII) collagen.

In one embodiment the invention features an isolated nucleic acid encoding a polypeptide substantially identical to human $\alpha 1$ (XVIII) collagen (SEQ ID NO:4). In a preferred embodiment the nucleic acid encodes human $\alpha 1$ (XVIII) collagen (SEQ ID NO:4).

In a related aspect the invention features a plasmid which includes the isolated nucleic acid. In a preferred embodiment the plasmid includes an expression control sequence capable of directing expression of the $\alpha 1$ (XVIII) collagen polypeptide.

In another related aspect the invention features a cell which includes the isolated nucleic acid. In various preferred embodiments the cell is a prokaryotic cell, a eukaryotic cell, and a mammalian cell. In a related aspect, the invention features a polypeptide produced by a cell which includes the isolated nucleic acid.

In another related aspect the invention features a polypeptide encoded by the isolated nucleic acid.

In another aspect the invention features an antibody generated against all or an immunogenic portion of human $\alpha 1$ (XVIII) collagen, which antibody is capable of specifically forming an immune complex with human $\alpha 1$ (XVIII) collagen. The invention also features portions of such antibodies which are capable of forming an immune complex with human $\alpha 1$ (XVIII) collagen.

The invention also features a substantially pure polypeptide having an amino acid sequence which is at least 80% identical to the amino acid sequence of human $\alpha 1$ (XVIII) collagen (SEQ ID NO:4). In preferred embodiment the polypeptide has an amino acid sequence which is at least 90% identical to the amino acid sequence of human $\alpha 1$ (XVIII) collagen (SEQ ID NO:4). In a more preferred embodiment the invention features a polypeptide having an amino acid sequence which is at least 95% identical to the amino acid sequence of human $\alpha 1$ (XVIII) collagen (SEQ ID NO:4). In a still more preferred embodiment the polypeptide is a human $\alpha 1$ (XVIII) collagen. In another preferred embodiment the polypeptide of claim 15 has the amino acid sequence of SEQ ID NO:4.

In a related aspect the invention features a therapeutic composition which includes, in a pharmaceutically-acceptable carrier, a substantially pure polypeptide having an amino acid sequence which is at least 80% identical to the amino acid sequence of human $\alpha 1$ (XVIII) collagen (SEQ ID NO:4).

In a related aspect the invention features a therapeutic composition which includes a drug and a human $\alpha 1$ (XVIII) collagen polypeptides as a carrier for the drug. In a preferred embodiment the drug is a protein.

The invention also features a method for treating a patient suffering from a disease associated with degradation of cartilage. The method includes administering to the patient a therapeutic composition which includes human $\alpha 1$ (XVIII) collagen. The invention also features a method for supplementing collagen in a patient in need of such supplementation. The method includes administering a therapeutic composition which includes human $\alpha 1$ (XVIII) collagen.

In another aspect the invention features a method for detecting human $\alpha 1$ (XVIII) collagen in a biological sample. The method includes contacting the sample with the antibody capable of forming an immune complex with human $\alpha 1$ (XVIII) collagen. In a preferred embodiment, the antibody is detectably labelled. In another preferred embodiment the antibody is detected with a second antibody which is capable of binding the first antibody.

In another aspect the invention features a method for detecting the presence of nucleic acid encoding human $\alpha 1$ (XVIII) collagen in a biological sample. The method includes the step of contacting the sample with the isolated nucleic acid described above and detecting the presence of said nucleic acid.

By "isolated" is meant that the nucleic acid is largely free of the coding sequences of those sequences that, in the naturally occurring genome of the organism from which the nucleic acid is derived, directly flank the nucleic acid. Isolated nucleic acid may be genomic DNA, cDNA, chemically synthesized nucleic acid, enzymatically synthesized nucleic acid, or recombinant nucleic acid. The term includes chemically synthesized nucleic acid and enzymatically synthesized nucleic acid produced using a recombinant nucleic acid as a template. By "plasmid" is meant an extrachromosoman DNA molecule which includes sequences that permit replication within a particular host cell. By "expression control sequence" is meant a nucleotide sequence which includes recognition sequences for factors that control expression of a protein coding sequence to which it is operably linked. Accordingly, an expression control sequence generally includes sequences for controlling both transcription and translation, for example, promoters, ribosome binding sites, and, optionally, repressor binding sites, and/or activator binding sites.

By a polypeptide "substantially identical" to human α1 (XVIII) collagen, is meant a polypeptide having an amino acid sequence which is at least 80% identical to the sequence of human α1 (XVIII) collagen (SEQ. ID. 4). Preferably the polypeptide is at least 85% identical to human α1 (XVIII) collagen, more preferably the polypeptide is at least 90% or 95% or even 99% identical to human α1 (XVIII) collagen. Identity for amino acid sequences refers to the match between two or more amino acid sequences. The percent identity of two given amino acid sequences, e.g., two proteins, is usually determined using sequence analysis software (e.g., the Sequence Analysis Software Package of the Genetics Computer Group, University of Wisconsin, Madison, Wis.). Such software determines the percentage of identical amino acids in two amino acid sequences that have been aligned so as to maximize identity. In determining the percent identity gaps are sometimes permitted. Differences between two polypeptide sequences that are substantially identical are preferentially conservative substitutions, i.e., one acidic amino acid is substituted for another acidic amino acid.

By "substantially pure" is meant a polypeptide or protein which has been separated from components (e.g., other proteins) with which it is normally found. Typically, a protein or polypeptide of interest is substantially pure when at least 75% of the polypeptide in a sample is the protein or polypeptide of interest. However, higher levels of purity are also desirable, e.g., 80%, 90%, 95%, 99%, or even 99.99% pure. By the term "capable of forming a specific immune complex" is meant an antibody which binds to the protein with which it forms an immune complex and which binds other proteins only very weakly if at all.

Besides essentially full-length α1 (XVIII) collagen, the present invention provides fragments of α1 (XVIII) collagen. As used herein, the term "fragment", as applied to collagen α1 (XVIII), will ordinarily be about 10, 15, or 20 contiguous amino acids and will preferably be at least 30 or at least 50 or 100 contiguous amino acids. Such fragments may be included in larger polypeptides. Multiple collagen α1 (XVIII) fragments may be combined in a single polypeptide.

Because α1 (XVIII) collagen has ser-gly sequences that conform to the consensus sequence for attachment sites found in proteoglycan core protein, this collagen can likely accept such side chains.

The addition of glycosaminoglycans can make type α1 (XVIII) collagen a better carrier for fibroblast growth factor (FGF) and other drugs which can associate with negatively charged molecules. Compositions which include type α1 (XVIII) collagen (with or without modification) and growth factors such as FGF can be used as for controlled delivery of growth factor to wounds (including burns) by implanting the composition into the wound. Further, because glycosaminoglycans are hydrophilic, addition of glycosaminoglycans to type α1 (XVIII) collagen can impart greater tensile strength to compositions which include such modified type α1 (XVIII) collagen.

Type α1 (XVIII) collagen can be used as a connective tissue filler in much the same fashion as type I collagen has been used. Such connective tissue fillers are useful both in plastic surgery and in the field of dermatology. Type α1 (XVIII) collagen may be interposed between a dermal equivalents and skin in order to improve adhesion. Alternatively, type α1 (XVIII) collagen can be used as a substrate on which to grow epithelium which can then be used as a replacement for damaged tissue.

BRIEF DESCRIPTION OF THE DRAWING

FIGS. 2A–2H is a representation of the nucleotide and corresponding amino acid sequence (SEQ ID No: 1) of nearly all of murine α1 (XVIII). Triple-helical regions are underlined. The imperfections in Gly-X-Y repeats are underlined by double lines. Cysteinyl residues are indicated by dots. Potential glycosaminoglycan attachment sites and N-linked glycosyaminoglycan sites are indicated by a series of Λ.

FIG. 4 is a comparison of amino acid sequences within the carboxyl ⅔ of the carboxyl non-triple-helical (NC1) domain of mouse α1 (XVIII) (SEQ ID NO: 2) and human α1 (XV) collagen (SEQ ID NO: 3) chains. Identical residues are indicated by vertical lines, and similar residues are indicated by asterisks. To obtain the best alignment, a gap is introduced (–). Four crysteinyl residues are marked with dots. The termination of translation is indicated by %.

FIGS. 6A–6F is a representation of the nucleotide sequence of human cDNA clones isolated and the derived amino acid sequence of human α1 (XVIII) collagen (SEQ ID NO:4). The sequences defining triple-helical domains are underlined. Five imperfections in Gly-X-Y repeats are underlined by double lines. The 5' boundaries of 4 identified exons are indicated by arrowheads pointing to the right, placed above the most 5' nucleotide of the exon; the 3' boundaries of these exons are indicated by arrowheads pointing to the left, placed above the most 3' nucleotide of the exon. Four cysteinyl residues are indicated by bold letters and the two poly-adenylation sites are underlined by a series of Λ. The translation stop codon is indicated by an asterisk.

FIG. 8 is a schematic representation of the segregation of Col8α1 among mouse chromosome 10 loci in [(C3H/HeJ-gld x *M. spretus*)F1 ×C3H/HeJ-gld] interspecific backcross mice. Filled boxes represent the homozygous C3H pattern and open boxes the F1 pattern.

DESCRIPTION OF THE PREFERRED EMBODIMENTS

Figure 1A:
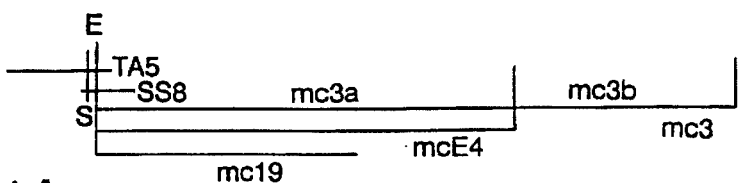
FIG. 1: panel A is a schematic representation of the clones (TA5, SS8, Mc3 (which includes mc3a and mc3b), McE4, and mc19) used to determine the sequence of murine α1 (XVIII) collagen. "E" indicates the position of EcoRI sites and "S" indicates the position of a SmaI site. Panel B is a schematic representation of murine collagen α1 (XVIII). Triple-helical domains are indicated by rectangular areas; non-triple-helical regions are indicated by heavy lines. Numbers indicated the length (in amino acid residues) of the domains. Where the domain sizes of the human protein differs from that of the murine protein, the human domain in parentheses above the murine size. Panel C is a schematic representation of the domain structure of the carboxyl half of human α1 (XV) collagen and the overlapping cDNA clones (YMh46, YMh4, Ykh17-2, Ykh17-1) used to determine the sequence of a portion of human collagen α1 (XV) chain. Triple-helical domains are indicated by rectangular areas; non-triple-helical regions are indicated by heavy lines. Numbers indicated the length (in amino acid residues) of the domains.

Described below is the cloning and sequencing of a human and a murine cDNA encoding a novel collagenous polypeptide, collagen α1 (XVIII). Collagen α1 (XVIII) has 10 triple-helical domains of the type commonly found in collagens. These domains are separated and flanked by non-triple-helical regions which may provide flexibility. Within the non-triple-helical regions are several -Ser-Gly-containing sequences that conform to the consensus sequences of glycosaminoglycan attachment sites in proteoglycan core proteins (see Bourdon, in Extracellular Matrix Genes, Sandell et al. eds., Academic Press, San Diego, p. 157). The collagen α1 (XVIII) gene is expressed in multiple organs. The highest levels of RNA are in liver, lung, and kidney as detected by Northern blots.

Murine α1 (XVIII) Collagen

Screening of cDNA Libraries and Nucleotide Sequencing:

Murine α1 (XVIII) collagen cDNAs were isolated by screening two commercial cDNA libraries. The first library contained cDNA synthesized with RNA isolated from 15.5-day old mouse embryos and cloned into the EcoRI site of λgt10 (Clontech, Palo Alto, Calif.). A 1.3 kb HindIII/EcoRI-Fragment of the murine type XII collagen cDNA mXIIc5 was used as probe (Oh et al., *Genomics* 14:225, 1992). One positive clone, mc19, containing a 1.5 kb insert, was isolated and characterized.

The second library contained cDNA synthesized with RNA isolated from 17.5-day old mouse embryos and cloned into the EcoRi site of λgt11 (Clontech) and was screened using as probe a 0.5 kb EcoRI/ApaI-fragment from the 5' region of mc19. This led to the isolation of the clone mcE4, containing a 2.4 kb insert. This λgt11 library was also screened with a 2.0 kb PstI-fragment of the human cDNA hc1-1 encoding 3' portion of α1 (XVIII) as probe (see below) leading to the isolation of a third mouse cDNA, mc3, with a 3.7 kb insert.

For screening of the libraries the filters were hybridized at 65° C. overnight in 5×SSC, 1% Sarkosyl, and 100 µg/ml of salmon sperm DNA. The filters were washed twice in 3×SSC at 65° C. with 0.5% Sarkosyl and twice without Sarkosyl.

A human placenta cDNA library in λgt11 (Clontech) was used to isolate cDNAs encoding α1 (XV) collagen. Two probes were used for screening. One probe was a cDNA fragment encoding an unidentified collagenous protein. A second probe was a 550 bp-long EcoRI/ApaI fragment from the 5' end of the insert of the α1 (XVIII) cDNA mc19. This led to the isolation of the cDNAs YMh46, YMh4, YKh17-1 and YKh17-2. Screening with the unidentified probe was done by hybridizing filters at 42° C. overnight in 0.8M NaCl, 0.02M PIPES (pH 6.5), 20% formamide, 1% SDS, and 100 ug/ml of salmon sperm DNA. The filters were washed three times at 65° C. with 0.2×SSC, 1% SDS. Screening with the mc19 probe was done by hybridizing filters at 68° C. with 0.5% Sarkosyl and twice without Sarcosyl.

pBluescript plasmid vectors (Stratagene, La Jolla, CA) and M13 mp18 and mp19 vectors were used for subcloning. Nucleotide sequence analysis was performed with the dideoxy nucleotide chain-termination method (Sanger et al., *Proc. Natl. Acad. Sci. USA* 74:5463, 1977).

mRNA preparation and 5'RACE Procedures:

Livers were dissected from 2 month old mice (C57BL/6J). Total liver RNA was prepared using the guanidine isothiocyanate method (Chirgwin et al., *Biochemistry* 18:5294, 1979) and poly(A)+ RNA was enriched using an oligo-dT column from the Fastrack 2.0 kit (Invitrogen) 5'RACE procedures were slightly modified from Frohman et al. (in PCR Protocols: A Guide to Methods and Applications, Innis et al., eds., Academic Press, New York, p. 28). Briefly, 2 µg of poly(A)+RNA were used to synthesize first strand cDNA using random primers and AMV reverse transcriptase (USB) at 42° C. for 20 minutes. Primers were removed with Centricon 100 (Amicon Corp.), and dATP and terminal transferase (BRL) were added. The sample was incubated at 37° C. for 5 minutes to allow attachment of dA to the 5' end of the first strand cDNA. This dA-cDNA was used as template to amplify the 5' region of α1 (XVIII) collagen mRNA by PCR. Adaptor primer (17 mer) containing XhoI, SalI and ClaI restriction enzyme sites, adaptor-(dT)$_{17}$ (Frohman, in PCR Protocols: A Guide to Methods and Applications, Innis et al., eds., Academic Press, New York, p. 28, and specific antisense primers: PS1 (5'TGTGTGACTTGCTGCTTT3') (Seq. ID No. 5), ps3 (5'TAGCTCCAGTCCCTGCGA3') (Seq. ID No. 6), PS4 (5'CCGAGCAAATGGCACCCT3') (Seq. ID No. 7) were synthesized on a Cyclone Plus oligonucleotide synthesizer (Milligen, U.S.A./).

Figure 1B:
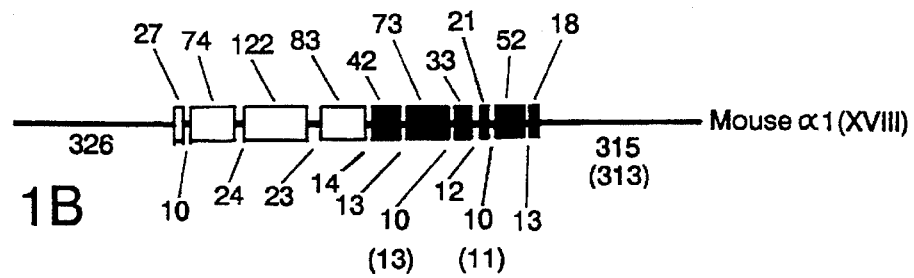
Figure 1C:
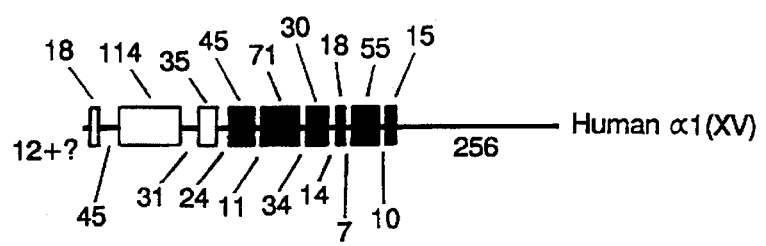

Second strand cDNA was synthesized with an aliquot of dA-cDNA using the adaptor-(dT)$_{17}$ primer and Taq DNA polymerase. Initial denaturation at 94° C. for 3 minutes was followed by annealing at 55° C. and 37° C. for 5 minutes each and extension at 72° C. for 40 minutes. The specific primer PS1 was added to the reaction and 30 cycles of first round PCR was performed; initial denaturation at 94° C. for 3 minutes was followed by annealing at 42° C. for 90 seconds, extension at 72° C. for 150 seconds and denaturation at 94° C. for 45 seconds. One tenth of the first round PCR products was used for second round nested PCR using the adaptor primer and PS2. The PCR conditions were the same as for the first round except that the annealing temperature was 52° C. instead of 42° C. The nested PCR products were cut with the restriction enzymes SmaI and SalI and subcloned into pBluescript. The subclones were screened by Southern blotting, using as probe a 145-bp EcoRI/SmaI fragment of mc19 (FIG. 1, panel A). One positive clone, SS8, contained a sequence matching that of the 5' region of mc19 and extending 70 bp further in the 5' direction. The specific primers PS3 and PS4 were used for first and nested PCR using the strategy described above. A major PCR product was obtained, purified by agarose gel electrophoresis, and subcloned into the modified EcoRV site of pBluescript (EcoRV cut pBluescript was incubated at 72° C. for 1 hour with Taq DNA polymerase and dTTP). One clone, TA5, contained the 70 bp of sequence of the 5' region of SS8, and extended 530 nucleotides further in the 5' direction.

Southern and Northern Hybridization:

Filters containing DNA or mRNA were hybridized with probes labeled with the random-primer labeling method (Boehringer-Mannheim) at 42° C. overnight in 50% formamide, 6×SSC, 5% dextran sulfate, 1 mM EDTA, 0.5% SDS, 25 µg/ml salmon sperm DNA, 1×Denhardt solution. Filters were washed three times (5 minuets each time) in 2×SSC, 0.1% SDS and then 4 times (15 minutes each time) in 0.2×SSC, 0.2% SDS. The concentration of probe was $2 \times 10^5$ cpm and $1 \times 10^6$ cpm per ml of hybridization solution for Southern and Northern hybridization, respectively.

Primary Structure of α1 (XVIII) Collagen:

Nucleotide sequencing of mc19 revealed that it encoded part of a polypeptide containing several triple-helical domains separated by non-triple-helical sequences (FIG. 1, panel B). A search for similarity with existing sequences indicated that it was different from all known types of collagen. Since mc19 contained an open reading frame without a translation start or stop codon, it was used as a probe to isolate overlapping cDNAs that would extend the reading frame in both 5' and 3' directions. As described above, screening of both mouse and human libraries led to the isolation of two additional overlapping mouse cDNAs (FIG. 1, panel A). The mouse cDNAs, mc19, mcE4, and mc3 have a common 5' end but vary in their lengths. The common 5' end coincides with the 5' EcoRI cloning site; this EcoRI site is an internal site in the α1 (XVIII) sequence. The sequence of mc19 and mcE4 are contained within the sequence of mc3, except for an about 70 nucleotide A-rich sequence at the 3' end of mc19, which probably represents a cloning artefact.

Preliminary sequence analysis showed that mc3 encodes the carboxyl end of the α1 (XVIII) translation product. To extend the sequence in the 5' direction we used 5' RACE with RNA isolated from mouse liver. This led to the isolation of the cDNAs SS8 and TA5. SS8 spans the EcoRI site at the 5' end of mc19, mcE4, and mc3; TA5 extends the sequence further in the 5' direction.

The sequence of the overlapping cDNAs appears to encode nearly all of the murine α1 (XVIII) collagen chain. Based on the size of murine α1 (XVIII) collagen, it appears that the cDNA sequence is not complete at the amino terminus of the protein.

Figure 3A:
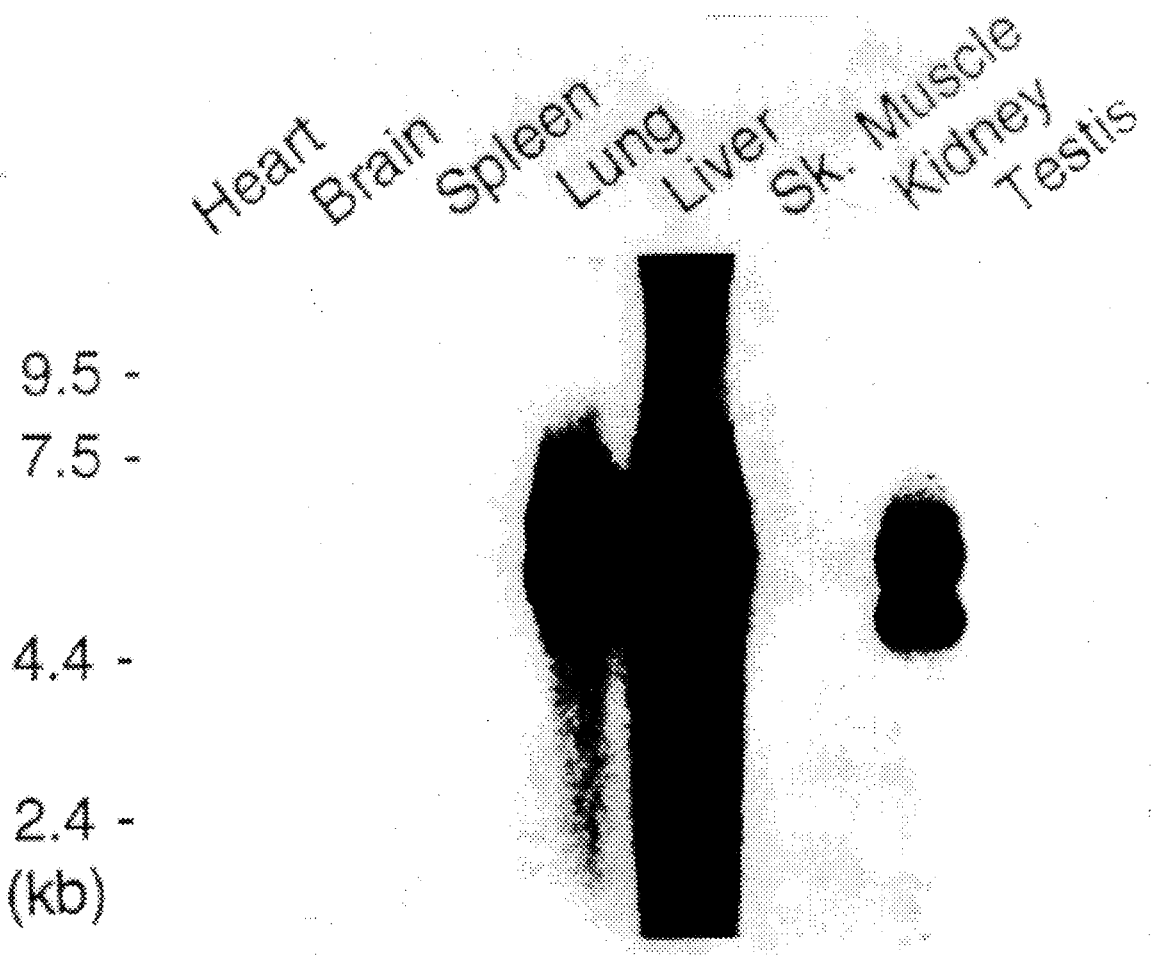
FIG. 3: panel A is a photograph of the results of a Northern blot showing that α1 (XVIII) transcripts are present in multiple organs. The mc3b probe recognizes two bands (4.5 and 5.5 kb) in heart, brain, spleen, kidney, and testis. The two bands in lung and liver have a lower mobility than the two bands in other tissues. Panel B is a photograph of the results of the same Northern blot as in panel A except with a shorter exposure time the hybridized filter is exposed for a short period of time to demonstrate these differences more clearly. In brain, a third band is migrating slightly above the 5.5 kb band.
Figure 3B:

The amino acid sequence of α1 (XVIII) collagen and the corresponding nucleotide sequence is shown in FIG. 3. Also included are 155 nucleotides of 3' untranslated sequence and a short poly A-tail.

The sequence defines ten domains of Gly-X-Y repeats (COL domains), which are separated and flanked by non-triple-helical regions (NC domains). The COL domains, numbered from the carboxyl end of the polypeptide chain, vary in length from 18 amino acid residues (COL1) to 122 amino acid residues (COL8). Because of imperfections in the Gly-X-Y triplet structure (FIG. 3) their lengths are not always an integral number of triplets. The NC-domains are also quite variable in length. The NC3 and NC10 domains are the shortest, with 10 amino-acid residues, while the carboxyl domain NC1 domain contains 317 amino acid residues.

Potential Glycosylation Sites in α1 (XVIII) Collagen:

Within the α1 (XVIII) collagen sequence there are two potential N-linked glycosylation sites. One site is in the amino-terminal NC11 domain and the other is in COL8 (FIG. 3). In addition, six Ser-Gly sequences are potential attachment sites for glycosaminoglycan chains (FIG. 3) since they are located within consensus sequence contexts for glycosaminoglycan side chains in proteoglycan core proteins (Bourdon, in *Extracellular Matrix Genes*, Sandell et al. eds., Academic Press, San Diego, Calif., p. 157). If these sequences are indeed utilized for attachment of glycosaminoglycans, α1 (XVIII) collagen would be an additional member of a growing group of collagen-proteoglycans, including types IX, XII, and XIV collagens (Irwin et al., *J. Biol. Chem.* 261:16281 1986; Watt et al., *J. Biol. Chem.* 267:20093, 1992; Brucker et al., *Proc. Natl. Acad. Sci. USA* 83:2608, 1985; Kock et al. *Eur. J. Biochem.* 207:847, 1992). Also α1 (XV) collagen contains potential sites for N- and O-linked glycosylation (Myers et al., *Proc. Natl. Acad. Sci. USA* 89:10144, 1992).

α1 (XVIII) Collagen mRNA is Expressed in Several Internal Organs:

Northern blot analysis with RNA from several different mouse tissues (Multiple Tissue Northern Blot, Cloutech) demonstrated that liver, lung and kidney contain the highest levels of α1 (XVIII) mRNA (FIG. 4). The mRNA migrates as two or three transcript bands, depending on the tissue source. In testis, kidney, spleen, brain, and heart one transcript is about 4.5 kb and a second transcript is 5.5 kb. In the brain a third band observed above the 5.5 kb band. In human two different size α1 (XVIII) transcripts are generated due to utilization of alternative polyadenylation signals (see below). Since the pattern of two different size transcripts in mouse tissues are similar to that in human tissues, it is likely that these two major bands are also produced by alternative polyadenylation of transcripts. Two major bands are also seen in liver and lung, but they have a slightly lower mobility than the two bands seen in the kidney. Northern blots of RNAs extracted from whole skeletons of 1 day-old mouse pups showed detectable α1 (XVIII) collagen transcripts, while skin extracts showed almost undetectable levels.

α1(XVIII) and α1 (XV) Collagen belong to a Novel Subfamily of Collagens:

The domain organization of α1 (XVIII) collagen is different from most other known collagen types. Comparison with a recently defined human collagen chain, α1 (XV), (Myers et al., *Proc. Natl. Acad. Sci. USA* 89:10144, 1992), shows, however, that the length of the 6 most carboxyl-terminal triple-helical domains are almost identical in α1 (XV) collagen and α1 (XVIII) collagen. In fact, they differ in size only by one amino acid triplet. In the 5' direction, beyond the six domains, the two chains are quite different. Thus, the mouse α1 (XVIII) chain contains four additional amino-terminal triple-helical domains of 27, 74, 122, and 83 amino acid residues, while human α1 (XV) contains three domains of 18, 114, and 35 amino acid residues in the same region (FIG. 1).

Screening of a human placenta cDNA library resulted in clones that extended into the 3' untranslated region of α1

(XV) (FIG. 1). A comparison of the amino acid sequences of α1 (XV) and α1 (XVIII) shows similarity within the carboxyl-terminal non-triple-helical domain NC1. In this region, the most carboxyl-terminal 177 amino acid residues are about 60% identical (comparing mouse α1 (XVIII) with human α1 (XV) at the amino acid level, with the locations of four cysteinyl residues conserved (FIG. 5)).

It appears then that α1 (XV) and α1 (XVIII) collagen chains are structurally, and perhaps functionally, related. The differences in the lengths of the non-triple-helical regions between the triple-helical domains and the difference in the amino-terminal portions, rule out the possibility that they represent two chains within the same type of collagen molecule. We suggest, therefore, that types XV and XVIII collagen are two members of a novel collagen subfamily, which we designate the MULTIPLEXIN family (for collagens with multiple triple-helix domains and interruptions). A common and distinguishing feature of members of this family would be a highly conserved carbosyl-terminal non-triple-helical domain. The high level of expression of α1 (XVIII) transcript in richly vascularized internal organs suggests that type XVIII collagen play a role in the perivascular extracellular matrix.

Human α1 (XVIII) Collagen

Isolation of cDNA clones:

A human placenta cDNA library (Clontech) was screened with a 600 bp SacI/EcoRI fragment of the murine α(1) XVIII collagen cDNA, mc8-1. The library filters were hybridized at 65° C. overnight in 5×SSC, 1% Sarkosyl (ICN), and 100 ug/ml of salmon sperm DNA (Overbeek et al., *Biochem. Biophys.* Acta 659:195, 1981). The filters were washed twice in 3×SSC at 65° C. with 0.5% Sarkosyl and twice without Sarkosyl. This led to the isolation of the cDNA clones he1-1, he9-1, and hc9-5.

Isolation of a genomic DNA clone:

A 1.7 kb ApaI fragment encoding the entire NC1 domain and 800 bp of the 3' untranslated sequence was isolated from the plasmid cDNA hc1-1. The fragment was used to screen a human genomic library in EMBL3 (Monaco et al., *Nature* 316:842, 1985). The genomic clone Nok3B2 was isolated. Exon containing restriction fragments from Nok3B2 were subcloned into pBluescript (Stratagene) and sequenced in each direction using T3 and T7 sequencing primers.

Northern blot analysis:

A human tissue blot (Clontech) was probed with a 2 kb PstI/EcoRI fragment of hc1-1. The region between the two putative polyadenylation signals in the cDNA was also used as probe. This second probe was generated using hc1-1 DNA as template for the polymerase chain reaction with the sense primer hN10 (5' -CATACTTTCCTGTATACT-3') (SEQ ID NO: 8) and the antisense primer hN12 (5'-CCTCAGCCACTTTGATGT-3') (SEQ ID NO: 9). Filters were hybridized at 42° C overnight in hybridization solution (6×SSC, 5×Denhardt's solution, 10% dextran sulfate, 1% SDS, and 100 µg/ml of salmon sperm DNA), and washed in 0.2×SSC and 2% SDS three times, for 5 minutes each time at room temperature, followed by washing with 0.1×SSC and 0.1% SDS three times, for 15 minutes each time at 58° C.

Subcloning and DNA sequence analysis:

pBluescript vectors (SK+; Stratagene) were used for subcloning. Nucleotide sequence analysis was performed with the dideoxy nucleotide chain-termination method.

Chromosomal mapping of the α1 (XVIII) collagen gene:

C3H/HeJ-gld and *Mus spretus* (Spain) mice and [C3H/HeJ-gld x *Mus spretus*) F1×C3H/HeJ-gld] interspecific backcross mice were bred and maintained as previously described (Seldin et al., *J. Exp. Med.* 167:688, 1988). *M. spretus* was chosen as the second parent because of the relative ease of detection of informative restriction fragment length variants (RFLVs) in comparison with crosses using conventional inbred laboratory strains.

DNA isolated from mouse organs was digested with restriction endonucleases and 10-µg samples were electrophoresed in 0.9% agarose gels. DNA was transferred to Nytran membranes, hybridized at 65° C., and washed under stringent conditions. A 900 bp-long EcoRI/BamHI fragment of mc19 was used as probe for the Coli8a1 gene. Other clones used as probes included pMC1 for the myb protooncogene (Myb), pSAm10b for the Col10a1 gene, and pAL1 for the Moloney leukemia virus integration site a (Minta). Gene linkage was determined by segregation analysis. Most likely gene order was determined by analyzing all haplotypes and minimizing crossover frequency between all genes.

Figure 5:
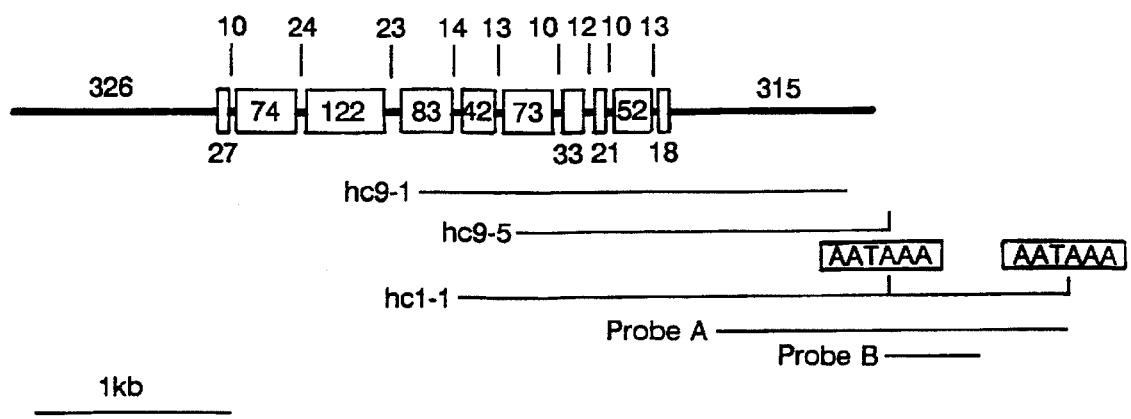
FIG. 5 is a schematic representation of the relative location of the three human cDNA clones (hc9-1, hc9-5, and hc1-1) used for sequence determination alongside a schematic representation of the domain structure of mouse α1 (XVIII) collagen. Non-triple-helical domains are indicated by a heavy line; triple-helical domains are indicated by boxed-in areas. The numbers show the lengths of the domains in amino acid residues. Probes A and B were used for the Northern blots. The positions of the two polyadenylation sites (AATAAA) are shown in hc1-1.

Fluorescent in situ hybridization:

Human metaphase chromosomes were prepared from normal PHA stimulated peripheral blood lymphocytes as described by Knoll et al., *Hum. Molec. Genet.* 2:183, 1993). Purified phage DNA from the genomic clone Nok3B2 was labelled by nick translation with biotin-16-dUTP (Boehringer-Mannheim). Hybridization and detection were performed with 150 ng of biotinylated phage DNA (Lawrence et al., *Science* 249:92, 1990). Hybridization signals were detected by fluoresceinated avidin (Vectro Laboratories, 5ug/ml) and viewed through a double bandpass filter (Omega Optical, Brattlebore, VT). Cells were mounted in a fluorescence antiface solution (Johnson et al., *J. Immunol. Methods* 43:349, 1989). For chromosome identification, cells were counterstained with 4'-6-diamidino-2-phenylindole (DAPI) and viewed with a DAPI filter (Zeiss) in a Zeiss Axiophot epifluorescence microscope. Cells were photographed on Kodak Ektar 1000 color film. Isolation of cDNA and genomic DNA fragments encoding human α1 (XVIII) collagen: Using a mouse α1 (XVIII) collagen cDNA fragment as probe, three human cDNA clones, hc1-1, hc9-1 and hc9-5, were isolated from a human placenta cDNA library (FIG. 5). The predicted translation product of the combined nucleotide sequences of the three clones defined a 3' untranslated sequence region, 7 triple-helical (COL) domains, and 7 non-triple-helical (NC) domains. FIGS. 6A–6F shows the cDNA sequence and the deduced amino acid sequence of human α1 (XVIII) collagen (SEQ ID NO: 4). Four cysteinyl residues in the carboxy-terminal non-triple-helical domain (NC1) and 5 imperfections in the Gly-X-Y triplet structure are perfectly aligned in the human and mouse sequences. The overall amino acid sequence identity is 81.6%. It is interesting to note that the COL2 domain of human α1 (XVIII) contains an additional triplet, and that one amino acid residue in NC3 and two amino acid residues in NC1 are missing in the human sequence, compared to the corresponding domains of mouse α1 (XVIII).

Figure 7A:
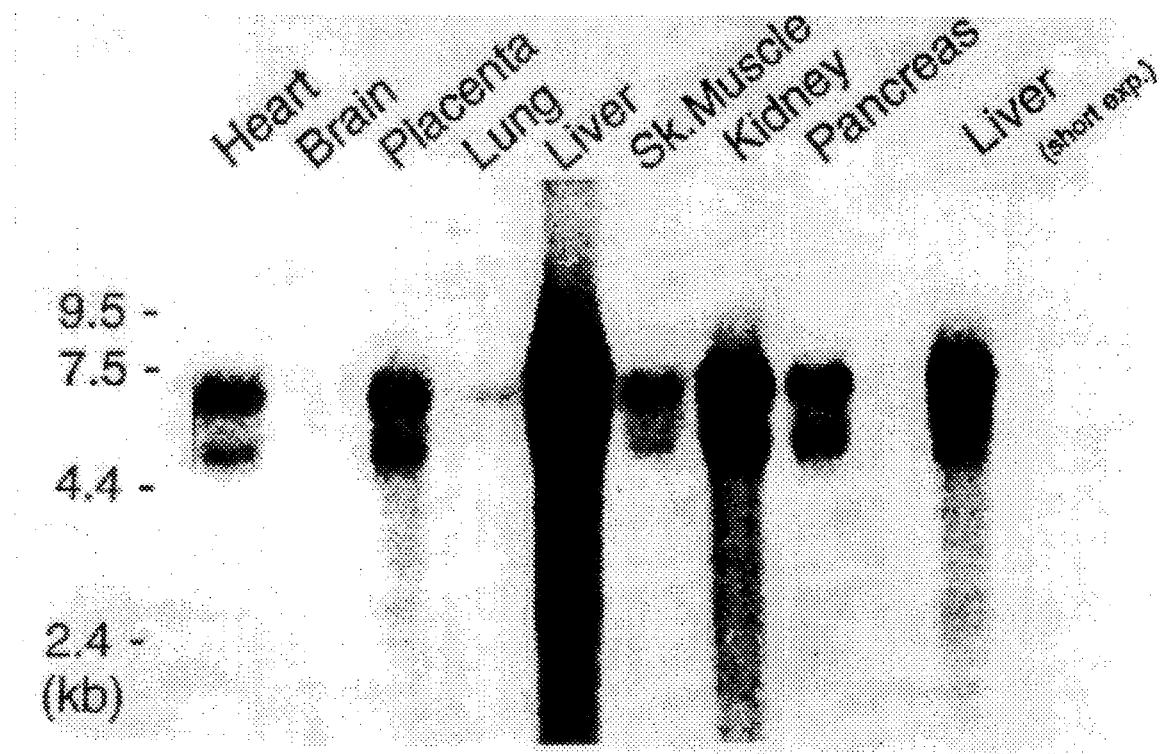
FIG. 7 is pair of a photographs illustrating of the results of a Northern blot showing that human α1 (XVIII) collagen transcripts are present in multiple organs. Panel A: Probe A recognizes two major bands around 5.0 kb and 6.0 kb. In the last lane (short exposure lane) an additional 6.5 kb band in liver RNA is observed. Panel B: Probe B recognizes only the 6.0 kb and 6.5 kb bands. The lane on the right was exposed to X-ray film for a short period of time, showing the 6.0 and 6.5 kb transcripts in liver RNA. On the left side the positions of RNA size markers are shown.
Figure 7B:
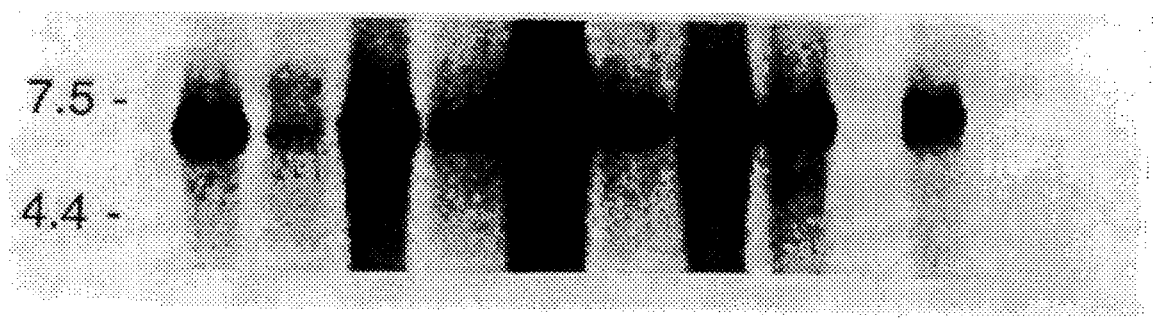

To isolate a genomic clone containing human α1 (XVIII) encoding exons and to locate the gene in the human chromosomes by FISH, we screened a human genomic library with a 1.7 kb ApaI fragment of the plasmid hc1-1. Screening of 5×10$^5$ plaques yielded a single positive phage clone, Nok3B2, containing a 16 kb insert. Southern blot analysis with hc1-1 following digestion of Nok3B2 DNA with either HingIII or PstI, identified 7 different non-overlapping hybridizing fragments ranging in size from 400 bp to 4 kb. Sequencing of 4 of these fragments allowed identification of 4 exons. The boundaries of these exons are indicated in FIGS. 6A–6F. With the 4 exons defined, the locations of 2 additional exons can be predicted. The 5' most exon encodes the junction between COL2 and NC2. The sizes of the 6 exons are all different, ranging from 33 nucleotides to 237 nucleotides. The 100% identity between the exon sequences and the α1 (XVIII) cDNA shows that the genomic clone NOK3B2 is part of the human gene, COL18A1, encoding α1 (XVIII) collagen.

α1 (XVIII) transcripts are present in multiple organs:

By Northern blot analysis, we found that the 3' half of hc1-1 (FIG. 7, panel A) hybridized to two major bands of about 5.0 and 6.0 kb. The two transcripts were present in multiple organs, with the highest levels in liver, kidney and placenta. The two transcripts were present at an equal ratio in all the organs. Interestingly, an additional 6.5 kb band was found in liver and brain. Since the hc1-1 cDNA contained two polydenylation signals (AATAAA) about 1 kb apart, we tested whether the difference between the 5.0 and 6.0 kb transcripts was due to the utilization of alternative poly-A sites. Using PCR, a cDNA segment between the two polyadenylation sites was amplified. This probe (FIG. 7, panel B) hybridized only to the upper bands (FIG. y, panel Z). Therefore, we conclude that the 5.0 kb band represents transcripts terminated at the most 5' poly-A site. Alternative poly-A signals have been found in other collagen genes such as COL1A2 (Myers et al., *J. Biol. Chem.* 258:10128, 1983), COL9A1 (Vasios, Ph.D. Thesis, Rutgers Medical School, 1986) and COL8A1 (Yamaguchi et al., *J. Biol. Chem.* 266:4508, 1991). The nature of the third 6.5 kb transcript present in liver and brain is not yet known.

Mapping of Col18 α1 to mouse chromosome 10 and COL8A1 to human chromosome 21:

For chromosomal mapping of the Col18α1 gene we used a panel of DNA samples from an interspecific backcross, previously characterized for several hundred genetic markers throughout the genome. Initially, DNA from the parental mice [C3H/HeJ-gld and (C3H/HeJ-gld x M. spretus)F1] were digested with various restriction endonucleases and hybridized with fragment of the cDNA mc19 to determine restriction fragment length variants that would allow haplotype analysis. Informative RFLVs were identified with the restriction endonuclease TaqI (C3H-gld showed 7.5, 3.5, and 2.6 kb bands; *M. spretus* showed 8.0, 4.6, and 2.3 kb bands).

Comparison of the distribution of the RFLVs indicated that in 113 of the 114 meiotic events examined, the Col18α1 locus co-segregated with Minta, a locus mapped to mouse chromosome 10 (FIG. 9). The distribution of haplotypes indicated the following gene order (±standard error): (centromere) Myb −7.0±2.4 cM −Col10α−25.4±4.1 cM −Col18α1−0.9±0.9−Minta, placing the Col18α1 locus close to the loci for Col6α1 and Col6α2 on chromosome 10 (Macdonald et al. 1992). Since α1 (VI) and α2 (VI) collagen genes are located on the human chromosome 21, it was likely that also the COL18A1 locus would be on the human chromosome 21.

This was confirmed by FISH analysis (FIG. 10). Using as probe DNA from the genomic clone Nok3B2 this analysis indicated that COL8A1 maps to chromosome 21q22.3. Twenty metaphases were examined and 18 of these revealed single or double chromatid hybridization at 21q22.3.

Preparation of α1 (XVIII) Collagen

α1 (XVIII) collagen can be prepared using bacterial or eukaryotic cells harboring a α1 (XVIII) collagen expressing plasmid. There are numerous expression vectors which can be used for preparing a α1 (XVIII) collagen expressing plasmid. Suitable expression vectors for eukaryotic cells include pXT1 and pSG5 (Stratagene Cloning Systems, La Jolla, Calif.). Suitable prokaryotic expression vectors include pNH8a, pN H16a, pNH18a, and pNH46a (Stratagene). α1 (XVIII) collagen encoding DNA can be inserted appropriately into any of these expression vectors (or other expression vectors) to create α1 (XVIII) expression plasmids which can be introduced into appropriate cells for production of α1 (XVIII) collagen. Preferably α1 (XVIII) collagen is produced in eukaryotic cells, e.g., cos cells, so that it can be modified properly, e.g., by the addition of glycocyamine-glycans. Fragments of α1 (XVIII) collagen can be prepared as described above by inserting a desired fragment of the α1 (XVIII) collagen gene into an expression vector.

α1 (XVIII) collagen can be purified using standard techniques. Techniques for protein purification are described in *Current Protocols in Molecular Biology* (John Wiley & Sons, New York, 1993). If α1 (XVIII) collagen is expressed in *E. coli* it can be expressed as a maltose binding protein fusion protein which can be purified using an amylose column. The purified fusion is the cleaved using a specific protease. This method permits rapid purification of proteins produced in *E. coli*. A kit for preparing and purifying fusion molecules is available from New England Biolabs (Beverly, Mass.).

Preparation of Antibodies Directed Against α1 (XVIII) Collagen and Uses Therefore Antibodies to α1 (XVIII) collagen polyclonal and monoclonal can be prepared using standard techniques (*Current Protocols in Molecular Biology*). Antibodies, preferably monoclonal, directed against α1 (XVIII) collagen can be used to purify α1 (XVIII) collagen using an immunoaffinity column. Such antibodies can also be used to detect α1 (XVIII) collagen in tissue samples. For example, antibodies can be used to detect abnormalities in α1 (XVIII) collagen metabolism. Immuno-assay methods which can employ antibodies directed against α1 (XVIII) collagen are described in *Current Protocols in Molecular Biology*.

Use

α1 (XVIII) collagen of fragments thereof may be used to prepare tissue substitutes and controlled drug delivery formulations. For example, a dermal equivalent can be produced by incorporating dermal fibroblasts into a three-dimensional matrix which is formed, at least in part, of α1 (XVIII) collagen.

α1 (XVIII) collagen can be used as a slow-release delivery vehicle for drugs, including growth factors, by mixing the drug of choice with iodine-gelled collagen or DOPA cross-linked collagen. The delivery vehicle is then implanted into a wound or at another location. DOPA cross-linked collagen, which can include α1 (XVIII) collagen or be composed exclusively thereof, can be used to repair bone or collagen.

α1 (XVIII) collagen can be used to treat diseases associated with erosion of bone or collagen, e.g, various forms of arthritis. In such an application α1 (XVIII) collagen can be injected into the site of erosion and can act as a substitute for the eroded bone or collagen. Similarly, α1 (XVIII) collagen can be used to treat diseases associated with the destruction of extracellular matrix.

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
( A ) LENGTH: 4031
( B ) TYPE: nucleic acid
( C ) STRANDEDNESS: single
( D ) TOPOLOGY: linear ( x i ) SEQUENCE DESCRIPTION: SEQ ID NO: 1:

| GAG | AAT | GTT | GCT | GAG | GAG | GTG | GGG | CTG | CTG | CAG | CTC | CTT | GGA | GAC | CCC | 48 |
|---|---|---|---|---|---|---|---|---|---|---|---|---|---|---|---|---|
| Glu | Asn | Val | Ala | Glu | Glu | Val | Gly | Leu | Leu | Gln | Leu | Leu | Gly | Asp | Pro | |
| 1 | | | | 5 | | | | | 10 | | | | | 15 | | |

| CTA | CCT | GAG | AAG | ATC | TCA | CAA | ATC | GAT | GAC | CCT | CAC | GTC | GGG | CCG | GCC | 96 |
|---|---|---|---|---|---|---|---|---|---|---|---|---|---|---|---|---|
| Leu | Pro | Glu | Lys | Ile | Ser | Gln | Ile | Asp | Asp | Pro | His | Val | Gly | Pro | Ala | |
| | | | 20 | | | | | 25 | | | | | 30 | | | |

| TAC | ATC | TTT | GGA | CCA | GAC | TCC | AAC | AGT | GGC | CAG | GTG | GCC | CAG | TAT | CAT | 144 |
|---|---|---|---|---|---|---|---|---|---|---|---|---|---|---|---|---|
| Tyr | Ile | Phe | Gly | Pro | Asp | Ser | Asn | Ser | Gly | Gln | Val | Ala | Gln | Tyr | His | |
| | | 35 | | | | | 40 | | | | | 45 | | | | |

| TTC | CCA | AAA | CTC | TTC | TTC | CGG | GAC | TTT | TCG | CTG | CTG | TTT | CAT | GTC | CGG | 192 |
|---|---|---|---|---|---|---|---|---|---|---|---|---|---|---|---|---|
| Phe | Pro | Lys | Leu | Phe | Phe | Arg | Asp | Phe | Ser | Leu | Leu | Phe | His | Val | Arg | |
| | 50 | | | | | 55 | | | | | 60 | | | | | |

| CCA | GCC | ACA | GAG | GCA | GCA | GGG | GTG | CTA | TTT | GCC | ATC | ACA | GAT | GCT | GCC | 240 |
|---|---|---|---|---|---|---|---|---|---|---|---|---|---|---|---|---|
| Pro | Ala | Thr | Glu | Ala | Ala | Gly | Val | Leu | Phe | Ala | Ile | Thr | Asp | Ala | Ala | |
| 65 | | | | 70 | | | | | 75 | | | | | | 80 | |

| CAG | GTG | GTA | GTC | TCA | CTG | GGC | GTG | AAG | CTC | TCA | GAG | GTC | CGA | GAT | GGA | 288 |
|---|---|---|---|---|---|---|---|---|---|---|---|---|---|---|---|---|
| Gln | Val | Val | Val | Ser | Leu | Gly | Val | Lys | Leu | Ser | Glu | Val | Arg | Asp | Gly | |
| | | | | 85 | | | | | 90 | | | | | 95 | | |

| CAG | CAA | AAC | ATC | TCA | TTG | CTC | TAC | ACG | GAG | CCT | GGG | GCC | AGC | CAG | ACC | 336 |
|---|---|---|---|---|---|---|---|---|---|---|---|---|---|---|---|---|
| Gln | Gln | Asn | Ile | Ser | Leu | Leu | Tyr | Thr | Glu | Pro | Gly | Ala | Ser | Gln | Thr | |
| | | | 100 | | | | | 105 | | | | | 110 | | | |

| CAG | ACG | GGA | GCC | AGC | TTC | CGC | CTA | CCT | GCA | TTT | GTT | GGG | CAG | TGG | ACA | 384 |
|---|---|---|---|---|---|---|---|---|---|---|---|---|---|---|---|---|
| Gln | Thr | Gly | Ala | Ser | Phe | Arg | Leu | Pro | Ala | Phe | Val | Gly | Gln | Trp | Thr | |
| | | 115 | | | | | 120 | | | | | 125 | | | | |

| CAC | TTC | GCG | CTC | AGC | GTC | GAC | GGA | GGC | TCT | GTG | GCT | CTC | TAC | GTA | GAC | 432 |
|---|---|---|---|---|---|---|---|---|---|---|---|---|---|---|---|---|
| His | Phe | Ala | Leu | Ser | Val | Asp | Gly | Gly | Ser | Val | Ala | Leu | Tyr | Val | Asp | |
| | 130 | | | | | 135 | | | | | 140 | | | | | |

| TGT | GAA | GAA | TTC | CAG | AGG | GTG | CCA | TTT | GCT | CGG | GCC | TCG | CAG | GGA | CTG | 480 |
|---|---|---|---|---|---|---|---|---|---|---|---|---|---|---|---|---|
| Cys | Glu | Glu | Phe | Gln | Arg | Val | Pro | Phe | Ala | Arg | Ala | Ser | Gln | Gly | Leu | |
| 145 | | | | 150 | | | | | 155 | | | | | 160 | | |

| GAG | CTA | GAG | CGT | GGC | GCT | GGC | CTC | TTT | GTG | GGT | CAG | GCT | GGA | ACA | GCA | 528 |
|---|---|---|---|---|---|---|---|---|---|---|---|---|---|---|---|---|
| Glu | Leu | Glu | Arg | Gly | Ala | Gly | Leu | Phe | Val | Gly | Gln | Ala | Gly | Thr | Ala | |
| | | | | 165 | | | | | 170 | | | | | 175 | | |

| GAC | CCT | GAC | AAG | TTC | CAG | GGG | ATG | ATC | TCA | GAG | CTG | AAG | GTA | CGC | AAA | 576 |
|---|---|---|---|---|---|---|---|---|---|---|---|---|---|---|---|---|
| Asp | Pro | Asp | Lys | Phe | Gln | Gly | Met | Ile | Ser | Glu | Leu | Lys | Val | Arg | Lys | |
| | | | 180 | | | | | 185 | | | | | 190 | | | |

| ACC | CCC | CGG | GTG | AGC | CCT | GTG | CAC | TGT | CTG | GAT | GAA | GAA | GAT | GAT | GAT | 624 |
|---|---|---|---|---|---|---|---|---|---|---|---|---|---|---|---|---|
| Thr | Pro | Arg | Val | Ser | Pro | Val | His | Cys | Leu | Asp | Glu | Glu | Asp | Asp | Asp | |
| | | 195 | | | | | 200 | | | | | 205 | | | | |

| GAA | GAC | CGG | GCA | TCT | GGA | GAT | TTT | GGA | AGT | GGC | TTT | GAA | GAA | AGC | AGC | 672 |
|---|---|---|---|---|---|---|---|---|---|---|---|---|---|---|---|---|
| Glu | Asp | Arg | Ala | Ser | Gly | Asp | Phe | Gly | Ser | Gly | Phe | Glu | Glu | Ser | Ser | |
| | 210 | | | | | 215 | | | | | 220 | | | | | |

| AAG | TCA | CAC | AAG | GAG | GAT | ACA | TCT | CTA | CTA | CCT | GGG | CTC | CCT | CAG | CCA | 720 |
|---|---|---|---|---|---|---|---|---|---|---|---|---|---|---|---|---|
| Lys | Ser | His | Lys | Glu | Asp | Thr | Ser | Leu | Leu | Pro | Gly | Leu | Pro | Gln | Pro | |
| 225 | | | | 230 | | | | | 235 | | | | | 240 | | |

| CCT | CCT | GTC | ACT | TCC | CCA | CCC | CTG | GCT | GGA | GGC | AGC | ACC | ACA | GAA | GAT | 768 |
|---|---|---|---|---|---|---|---|---|---|---|---|---|---|---|---|---|
| Pro | Pro | Val | Thr | Ser | Pro | Pro | Leu | Ala | Gly | Gly | Ser | Thr | Thr | Glu | Asp | |

-continued

|     |     |     |     |     |     | 245 |     |     |     |     |     | 250 |     |     |     |     |     | 255 |     |     |      |
|-----|-----|-----|-----|-----|-----|-----|-----|-----|-----|-----|-----|-----|-----|-----|-----|-----|-----|-----|-----|-----|------|
| CCT | AGA | ACA | GAA | GAA | ACG | GAG | GAA | GAC | GCC | GCG | GTA | GAT | TCT | ATA | GGA | | | | | | 816 |
| Pro | Arg | Thr | Glu | Glu | Thr | Glu | Glu | Asp | Ala | Ala | Val | Asp | Ser | Ile | Gly | | | | | | |
| | | | 260 | | | | | 265 | | | | | 270 | | | | | | | | |

| GCT | GAG | ACC | CTT | CCT | GGC | ACA | GGT | TCA | AGC | GGT | GCA | TGG | GAT | GAG | GCT | 864 |
|-----|-----|-----|-----|-----|-----|-----|-----|-----|-----|-----|-----|-----|-----|-----|-----|-----|
| Ala | Glu | Thr | Leu | Pro | Gly | Thr | Gly | Ser | Ser | Gly | Ala | Trp | Asp | Glu | Ala | |
| | | 275 | | | | | 280 | | | | | 285 | | | | |

| ATC | CAG | AAC | CCC | GGA | AGG | GGC | TTG | ATA | AAG | GGA | GGT | ATG | AAA | GGA | CAA | 912 |
| Ile | Gln | Asn | Pro | Gly | Arg | Gly | Leu | Ile | Lys | Gly | Gly | Met | Lys | Gly | Gln | |
| | 290 | | | | | 295 | | | | | 300 | | | | | |

| AAG | GGA | GAA | CCA | GGT | GCC | CAG | GGC | CCA | CCT | GGC | CCA | GCT | GGC | CCC | CAG | 960 |
| Lys | Gly | Glu | Pro | Gly | Ala | Gln | Gly | Pro | Pro | Gly | Pro | Ala | Gly | Pro | Gln | |
| 305 | | | | 310 | | | | | 315 | | | | | 320 | | |

| GGT | CCT | GCC | GGT | CCA | GTG | GTC | CAG | AGC | CCC | AAC | TCA | CAA | CCT | GTC | CCT | 1008 |
| Gly | Pro | Ala | Gly | Pro | Val | Val | Gln | Ser | Pro | Asn | Ser | Gln | Pro | Val | Pro | |
| | | | | 325 | | | | | 330 | | | | | 335 | | |

| GGA | GCA | CAA | GGA | CCC | CCG | GGA | CCT | CAG | GGG | CCA | CCA | GGG | AAG | GAT | GGC | 1056 |
| Gly | Ala | Gln | Gly | Pro | Pro | Gly | Pro | Gln | Gly | Pro | Pro | Gly | Lys | Asp | Gly | |
| | | | 340 | | | | | 345 | | | | | 350 | | | |

| ACT | CCA | GGA | AGG | GAT | GGT | GAA | CCG | GGT | GAC | CCT | GGT | GAA | GAT | GGG | AGA | 1104 |
| Thr | Pro | Gly | Arg | Asp | Gly | Glu | Pro | Gly | Asp | Pro | Gly | Glu | Asp | Gly | Arg | |
| | | 355 | | | | | 360 | | | | | 365 | | | | |

| CCG | GGT | GAC | ACT | GGA | CCT | CAA | GGC | TTT | CCA | GGG | ACC | CCA | GGA | GAT | GTG | 1152 |
| Pro | Gly | Asp | Thr | Gly | Pro | Gln | Gly | Phe | Pro | Gly | Thr | Pro | Gly | Asp | Val | |
| | 370 | | | | | 375 | | | | | 380 | | | | | |

| GGC | CCT | AAG | GGC | GAG | AAG | GGA | GAT | CCT | GGT | ATT | GGG | CCC | CGA | GGA | CCT | 1200 |
| Gly | Pro | Lys | Gly | Glu | Lys | Gly | Asp | Pro | Gly | Ile | Gly | Pro | Arg | Gly | Pro | |
| 385 | | | | 390 | | | | | 395 | | | | | 400 | | |

| CCA | GGG | CCT | CCA | GGG | CCA | CCA | GGA | CCC | TCC | TTC | AGA | CAA | GAC | AAG | CTG | 1248 |
| Pro | Gly | Pro | Pro | Gly | Pro | Pro | Gly | Pro | Ser | Phe | Arg | Gln | Asp | Lys | Leu | |
| | | | | 405 | | | | | 410 | | | | | 415 | | |

| ACC | TTC | ATT | GAC | ATG | GAG | GGA | TCC | GGT | TTC | AGC | GGA | GAC | ATA | GAG | AGC | 1296 |
| Thr | Phe | Ile | Asp | Met | Glu | Gly | Ser | Gly | Phe | Ser | Gly | Asp | Ile | Glu | Ser | |
| | | | 420 | | | | | 425 | | | | | 430 | | | |

| CTT | AGA | GGC | CCA | CGA | GGC | TTC | CCT | GGC | CCC | CCG | GGG | CCC | CCT | GGT | GTC | 1344 |
| Leu | Arg | Gly | Pro | Arg | Gly | Phe | Pro | Gly | Pro | Pro | Gly | Pro | Pro | Gly | Val | |
| | | 435 | | | | | 440 | | | | | 445 | | | | |

| CCA | GGA | CTT | CCT | GGT | GAG | CCA | GGA | CGC | TTT | GGG | ATC | AAT | GGT | TCC | TAT | 1392 |
| Pro | Gly | Leu | Pro | Gly | Glu | Pro | Gly | Arg | Phe | Gly | Ile | Asn | Gly | Ser | Tyr | |
| | 450 | | | | | 455 | | | | | 460 | | | | | |

| GCA | CCA | GGA | CCT | GCA | GGC | CTT | CCT | GGT | GTA | CCT | GGG | AAG | GAA | GGA | CCC | 1440 |
| Ala | Pro | Gly | Pro | Ala | Gly | Leu | Pro | Gly | Val | Pro | Gly | Lys | Glu | Gly | Pro | |
| 465 | | | | 470 | | | | | 475 | | | | | 480 | | |

| CCC | GGT | TTT | CCA | GGT | CCC | CCG | GGA | CCT | CCA | GGT | CCT | CCA | GGC | AAA | GAG | 1488 |
| Pro | Gly | Phe | Pro | Gly | Pro | Pro | Gly | Pro | Pro | Gly | Pro | Pro | Gly | Lys | Glu | |
| | | | | 485 | | | | | 490 | | | | | 495 | | |

| GGC | CCA | CCA | GGA | GTG | GCC | GGC | CAG | AAA | GGC | AGT | GTT | GGT | GAT | GTG | GGC | 1536 |
| Gly | Pro | Pro | Gly | Val | Ala | Gly | Gln | Lys | Gly | Ser | Val | Gly | Asp | Val | Gly | |
| | | | 500 | | | | | 505 | | | | | 510 | | | |

| ATC | CCA | GGA | CCC | AAG | GGG | AGC | AAA | GGA | GAC | CTT | GGG | CCC | ATC | GGT | ATG | 1584 |
| Ile | Pro | Gly | Pro | Lys | Gly | Ser | Lys | Gly | Asp | Leu | Gly | Pro | Ile | Gly | Met | |
| | | 515 | | | | | 520 | | | | | 525 | | | | |

| CCT | GGC | AAG | TCT | GGC | TTG | GCT | GGA | TCC | CCT | GGG | CCA | GTT | GGA | CCC | CCA | 1632 |
| Pro | Gly | Lys | Ser | Gly | Leu | Ala | Gly | Ser | Pro | Gly | Pro | Val | Gly | Pro | Pro | |
| | 530 | | | | | 535 | | | | | 540 | | | | | |

| GGA | CCT | CCA | GGG | CCT | CCA | GGG | CCA | CCA | GGA | CCA | GGA | TTT | GCT | GCT | GGA | 1680 |
| Gly | Pro | Pro | Gly | Pro | Pro | Gly | Pro | Pro | Gly | Pro | Gly | Phe | Ala | Ala | Gly | |
| 545 | | | | 550 | | | | | 555 | | | | | 560 | | |

| TTC | GAT | GAT | ATG | GAA | GGC | TCT | GGA | ATA | CCC | CTC | TGG | ACA | ACA | GCC | CGA | 1728 |
| Phe | Asp | Asp | Met | Glu | Gly | Ser | Gly | Ile | Pro | Leu | Trp | Thr | Thr | Ala | Arg | |

-continued

|  |  | 565 |  |  |  |  | 570 |  |  |  |  | 575 |  |  |  |
|---|---|---|---|---|---|---|---|---|---|---|---|---|---|---|---|
| AGC | TCT | GAT | GGG | CTG | CAG | GGA | CCT | CCC | GGG | TCG | CCG | GGA | CTC | AAG | GGG |
| Ser | Ser | Asp | Gly | Leu | Gln | Gly | Pro | Pro | Gly | Ser | Pro | Gly | Leu | Lys | Gly |
|  |  | 580 |  |  |  |  | 585 |  |  |  |  | 590 |  |  |  | 1776

| GAT | CCT | GGA | GTG | GCA | GGC | CTA | CCT | GGA | GCC | AAG | GGA | GAA | GTT | GGA | GCA |
| Asp | Pro | Gly | Val | Ala | Gly | Leu | Pro | Gly | Ala | Lys | Gly | Glu | Val | Gly | Ala |
|  |  | 595 |  |  |  |  | 600 |  |  |  |  | 605 |  |  |  | 1824

| GAT | GGA | GCC | CAG | GGC | ATC | CCT | GGT | CCC | CCA | GGA | AGA | GAA | GGT | GCA | GCT |
| Asp | Gly | Ala | Gln | Gly | Ile | Pro | Gly | Pro | Pro | Gly | Arg | Glu | Gly | Ala | Ala |
|  |  | 610 |  |  |  |  | 615 |  |  |  |  | 620 |  |  |  | 1872

| GGA | TCT | CCG | GGG | CCA | AAA | GGA | GAG | AAG | GGG | ATG | CCG | GGA | GAA | AAG | GGA |
| Gly | Ser | Pro | Gly | Pro | Lys | Gly | Glu | Lys | Gly | Met | Pro | Gly | Glu | Lys | Gly |
| 625 |  |  |  |  | 630 |  |  |  |  | 635 |  |  |  |  | 640 | 1920

| AAC | CCA | GGA | AAA | GAT | GGA | GTG | GGC | CGG | CCG | GGC | CTC | CCT | GGG | CCT | CCA |
| Asn | Pro | Gly | Lys | Asp | Gly | Val | Gly | Arg | Pro | Gly | Leu | Pro | Gly | Pro | Pro |
|  |  |  |  | 645 |  |  |  |  | 650 |  |  |  |  | 655 |  | 1968

| GGA | CCT | CCA | GGG | CCT | GTG | ATC | TAT | GTG | TCA | AGT | GAG | GAT | AAA | GCA | ATA |
| Gly | Pro | Pro | Gly | Pro | Val | Ile | Tyr | Val | Ser | Ser | Glu | Asp | Lys | Ala | Ile |
|  |  |  | 660 |  |  |  |  | 665 |  |  |  |  | 670 |  |  | 2016

| GTG | AGC | ACG | CCA | GGA | CCT | GAG | GGC | AAG | CCA | GGG | TAC | GCA | GGC | TTT | CCT |
| Val | Ser | Thr | Pro | Gly | Pro | Glu | Gly | Lys | Pro | Gly | Tyr | Ala | Gly | Phe | Pro |
|  |  | 675 |  |  |  |  | 680 |  |  |  |  | 685 |  |  |  | 2064

| GGA | CCT | GCT | GGA | CCG | AAG | GGT | GAC | CTG | GGT | TCC | AAA | GGC | GAG | CAG | GGT |
| Gly | Pro | Ala | Gly | Pro | Lys | Gly | Asp | Leu | Gly | Ser | Lys | Gly | Glu | Gln | Gly |
|  |  | 690 |  |  |  |  | 695 |  |  |  |  | 700 |  |  |  | 2112

| CTT | CCG | GGG | CCC | AAG | GGT | GAG | AAG | GGA | GAG | CCA | GGC | ACT | ATC | TTT | AGT |
| Leu | Pro | Gly | Pro | Lys | Gly | Glu | Lys | Gly | Glu | Pro | Gly | Thr | Ile | Phe | Ser |
| 705 |  |  |  |  | 710 |  |  |  |  | 715 |  |  |  |  | 720 | 2160

| CCT | GAT | GGC | AGA | GCT | CTG | GGC | CAT | CCC | CAG | AAG | GGA | GCC | AAG | GGA | GAG |
| Pro | Asp | Gly | Arg | Ala | Leu | Gly | His | Pro | Gln | Lys | Gly | Ala | Lys | Gly | Glu |
|  |  |  |  | 725 |  |  |  |  | 730 |  |  |  |  | 735 |  | 2208

| CCA | GGC | TTT | CGA | GGA | CCC | CCG | GGT | CCT | TAT | GGA | CGA | CCT | GGG | CAC | AAG |
| Pro | Gly | Phe | Arg | Gly | Pro | Pro | Gly | Pro | Tyr | Gly | Arg | Pro | Gly | His | Lys |
|  |  |  | 740 |  |  |  |  | 745 |  |  |  |  | 750 |  |  | 2256

| GGT | GAA | ATT | GGC | TTC | CCT | GGA | CGG | CCG | GGT | CGA | CCT | GGA | ACG | AAT | GGC |
| Gly | Glu | Ile | Gly | Phe | Pro | Gly | Arg | Pro | Gly | Arg | Pro | Gly | Thr | Asn | Gly |
|  |  | 755 |  |  |  |  | 760 |  |  |  |  | 765 |  |  |  | 2304

| TTA | AAG | GGA | GAG | AAG | GGA | GAG | CCT | GGA | GAT | GCC | AGC | CTT | GGG | TTC | AGC |
| Leu | Lys | Gly | Glu | Lys | Gly | Glu | Pro | Gly | Asp | Ala | Ser | Leu | Gly | Phe | Ser |
| 770 |  |  |  |  | 775 |  |  |  |  | 780 |  |  |  |  |  | 2352

| ATG | AGG | GGA | TTG | CCT | GGC | CCC | CCT | GGG | CCT | CCA | GGA | CCC | CCA | GGT | CCT |
| Met | Arg | Gly | Leu | Pro | Gly | Pro | Pro | Gly | Pro | Pro | Gly | Pro | Pro | Gly | Pro |
| 785 |  |  |  |  | 790 |  |  |  |  | 795 |  |  |  |  | 800 | 2400

| CCT | GGG | ATG | CCC | ATC | TAT | GAC | AGC | AAT | GCA | TTT | GTG | GAG | TCT | GGC | CGA |
| Pro | Gly | Met | Pro | Ile | Tyr | Asp | Ser | Asn | Ala | Phe | Val | Glu | Ser | Gly | Arg |
|  |  |  |  | 805 |  |  |  |  | 810 |  |  |  |  | 815 |  | 2448

| CCT | GGA | CTA | CCA | GGA | CAG | CAG | GGT | GTG | CAG | GGG | CCT | TCA | GGA | CCA | AAG |
| Pro | Gly | Leu | Pro | Gly | Gln | Gln | Gly | Val | Gln | Gly | Pro | Ser | Gly | Pro | Lys |
|  |  |  | 820 |  |  |  |  | 825 |  |  |  |  | 830 |  |  | 2496

| GGT | GAC | AAA | GGA | GAG | GTG | GGC | CCA | CCT | GGG | CCA | CCA | GGG | CAA | TTC | CCC |
| Gly | Asp | Lys | Gly | Glu | Val | Gly | Pro | Pro | Gly | Pro | Pro | Gly | Gln | Phe | Pro |
|  |  | 835 |  |  |  |  | 840 |  |  |  |  | 845 |  |  |  | 2544

| ATT | GAC | CTC | TTC | CAC | CTG | GAA | GCG | GAA | ATG | AAG | GGG | GAC | AAG | GGA | GAC |
| Ile | Asp | Leu | Phe | His | Leu | Glu | Ala | Glu | Met | Lys | Gly | Asp | Lys | Gly | Asp |
|  | 850 |  |  |  |  | 855 |  |  |  |  | 860 |  |  |  |  | 2592

| CGA | GGG | GAT | GCT | GGA | CAG | AAA | GGA | GAG | AGG | GGA | GAA | CCT | GGG | GCT | CCT |
| Arg | Gly | Asp | Ala | Gly | Gln | Lys | Gly | Glu | Arg | Gly | Glu | Pro | Gly | Ala | Pro |
| 865 |  |  |  |  | 870 |  |  |  |  | 875 |  |  |  |  | 880 | 2640

| GGT | GGT | GGA | TTC | TTC | AGC | TCA | AGT | GTA | CCT | GGC | CCA | CCC | GGC | CCA | CCT |
| Gly | Gly | Gly | Phe | Phe | Ser | Ser | Ser | Val | Pro | Gly | Pro | Pro | Gly | Pro | Pro | 2688

|  |  |  |  |  |  |  |  |  |  |  |  |  |  |  |  |
|---|---|---|---|---|---|---|---|---|---|---|---|---|---|---|---|
|  |  |  | 885 |  |  |  |  | 890 |  |  |  |  | 895 |  |  |
| GGA | TAC | CCT | GGA | ATT | CCG | GGT | CCA | AAG | GGA | GAG | AGC | ATC | CGG | GGG | CCA | 2736 |
| Gly | Tyr | Pro | Gly | Ile | Pro | Gly | Pro | Lys | Gly | Glu | Ser | Ile | Arg | Gly | Pro |  |
|  |  |  | 900 |  |  |  |  | 905 |  |  |  |  | 910 |  |  |
| CCT | GGC | CCT | CCT | GGC | CCG | CAG | GGA | CCT | CCT | GGC | ATT | GGC | TAT | GAG | GGT | 2784 |
| Pro | Gly | Pro | Pro | Gly | Pro | Gln | Gly | Pro | Pro | Gly | Ile | Gly | Tyr | Glu | Gly |  |
|  |  |  | 915 |  |  |  |  | 920 |  |  |  |  | 925 |  |  |
| CGC | CAG | GGT | CCC | CCA | GGA | CCT | CCA | GGA | CCT | CCA | GGA | CCT | CCC | TCC | TTC | 2832 |
| Arg | Gln | Gly | Pro | Pro | Gly | Pro | Pro | Gly | Pro | Pro | Gly | Pro | Pro | Ser | Phe |  |
|  |  | 930 |  |  |  |  | 935 |  |  |  |  | 940 |  |  |  |
| CCT | GGC | CCT | CAC | AGA | CAG | ACT | GTC | AGT | GTT | CCT | GGT | CCT | CCG | GGC | CCA | 2880 |
| Pro | Gly | Pro | His | Arg | Gln | Thr | Val | Ser | Val | Pro | Gly | Pro | Pro | Gly | Pro |  |
| 945 |  |  |  |  | 950 |  |  |  |  | 955 |  |  |  |  | 960 |
| CCT | GGT | CCT | CCA | GGT | CCC | CCA | GGA | GCC | ATG | GGT | GCC | TCT | GCT | GGG | CAG | 2928 |
| Pro | Gly | Pro | Pro | Gly | Pro | Pro | Gly | Ala | Met | Gly | Ala | Ser | Ala | Gly | Gln |  |
|  |  |  |  | 965 |  |  |  |  | 970 |  |  |  |  | 975 |  |
| GTG | AGG | ATC | TGG | GCC | ACA | TAC | CAG | ACC | ATG | CTG | GAC | AAG | ATC | CGG | GAG | 2976 |
| Val | Arg | Ile | Trp | Ala | Thr | Tyr | Gln | Thr | Met | Leu | Asp | Lys | Ile | Arg | Glu |  |
|  |  |  | 980 |  |  |  |  | 985 |  |  |  |  | 990 |  |  |
| GTG | CCG | GAG | GGC | TGG | CTC | ATC | TTT | GTG | GCC | GAG | AGG | GAA | GAG | CTC | TAT | 3024 |
| Val | Pro | Glu | Gly | Trp | Leu | Ile | Phe | Val | Ala | Glu | Arg | Glu | Glu | Leu | Tyr |  |
|  |  |  | 995 |  |  |  |  | 1000 |  |  |  |  | 1005 |  |  |
| GTA | CGC | GTT | AGA | AAT | GGC | TTC | CGG | AAG | GTG | CTG | CTG | GAG | GCC | CGG | ACA | 3072 |
| Val | Arg | Val | Arg | Asn | Gly | Phe | Arg | Lys | Val | Leu | Leu | Glu | Ala | Arg | Thr |  |
|  |  |  | 1010 |  |  |  |  | 1015 |  |  |  |  | 1020 |  |  |
| GCC | CTC | CTG | AGA | GGC | ACG | GGC | AAT | GAG | GTG | GCT | GCT | TTC | CAG | CCC | CCA | 3120 |
| Ala | Leu | Leu | Arg | Gly | Thr | Gly | Asn | Glu | Val | Ala | Ala | Phe | Gln | Pro | Pro |  |
| 1025 |  |  |  |  | 1030 |  |  |  |  | 1035 |  |  |  |  | 1040 |
| TTG | GTC | CAG | CTT | CAT | GAG | GGC | AGT | CCA | TAC | ACC | CGG | AGG | GAG | TAC | TCC | 3168 |
| Leu | Val | Gln | Leu | His | Glu | Gly | Ser | Pro | Tyr | Thr | Arg | Arg | Glu | Tyr | Ser |  |
|  |  |  |  | 1045 |  |  |  |  | 1050 |  |  |  |  | 1055 |  |
| TAT | TCC | ACG | GCA | CGA | CCC | TGG | CGA | GCA | GAT | GAC | ATC | CTG | GCC | AAC | CCA | 3216 |
| Tyr | Ser | Thr | Ala | Arg | Pro | Trp | Arg | Ala | Asp | Asp | Ile | Leu | Ala | Asn | Pro |  |
|  |  |  |  | 1060 |  |  |  |  | 1065 |  |  |  |  | 1070 |  |
| CCG | CGC | CTG | CCA | GAC | CGC | CAG | CCT | TAC | CCT | GGA | GTT | CCA | CAT | CAC | CAC | 3264 |
| Pro | Arg | Leu | Pro | Asp | Arg | Gln | Pro | Tyr | Pro | Gly | Val | Pro | His | His | His |  |
|  |  |  | 1075 |  |  |  |  | 1080 |  |  |  |  | 1085 |  |  |
| AGT | TCC | TAT | GTG | CAC | CTG | CCG | CCA | GCC | CGC | CCC | ACC | CTC | TCA | CTT | GCT | 3312 |
| Ser | Ser | Tyr | Val | His | Leu | Pro | Pro | Ala | Arg | Pro | Thr | Leu | Ser | Leu | Ala |  |
|  |  |  | 1090 |  |  |  |  | 1095 |  |  |  |  | 1100 |  |  |
| CAT | ACT | CAT | CAG | GAC | TTT | CAG | CCA | GTG | CTC | CAC | CTG | GTG | GCA | CTG | AAC | 3360 |
| His | Thr | His | Gln | Asp | Phe | Gln | Pro | Val | Leu | His | Leu | Val | Ala | Leu | Asn |  |
| 1105 |  |  |  |  | 1110 |  |  |  |  | 1115 |  |  |  |  | 1120 |
| ACC | CCC | CTG | TCT | GGA | GGC | ATG | CGT | GGT | ATC | CGT | GGA | GCA | GAT | TTC | CAG | 3408 |
| Thr | Pro | Leu | Ser | Gly | Gly | Met | Arg | Gly | Ile | Arg | Gly | Ala | Asp | Phe | Gln |  |
|  |  |  |  | 1125 |  |  |  |  | 1130 |  |  |  |  | 1135 |  |
| TGC | TTC | CAG | CAA | GCC | CGA | GCC | GTG | GGG | CTG | TCG | GGC | ACC | TTC | CGG | GCT | 3456 |
| Cys | Phe | Gln | Gln | Ala | Arg | Ala | Val | Gly | Leu | Ser | Gly | Thr | Phe | Arg | Ala |  |
|  |  |  |  | 1140 |  |  |  |  | 1145 |  |  |  |  | 1150 |  |
| TTC | CTG | TCC | TCT | AGG | CTG | CAG | GAT | CTC | TAT | AGC | ATC | GTG | CGC | CGT | GCT | 3504 |
| Phe | Leu | Ser | Ser | Arg | Leu | Gln | Asp | Leu | Tyr | Ser | Ile | Val | Arg | Arg | Ala |  |
|  |  |  | 1155 |  |  |  |  | 1160 |  |  |  |  | 1165 |  |  |
| GAC | CGG | GGG | TCT | GTG | CCC | ATC | GTC | AAC | CTG | AAG | GAC | GAG | GTG | CTA | TCT | 3552 |
| Asp | Arg | Gly | Ser | Val | Pro | Ile | Val | Asn | Leu | Lys | Asp | Glu | Val | Leu | Ser |  |
|  |  |  | 1170 |  |  |  |  | 1175 |  |  |  |  | 1180 |  |  |
| CCC | AGC | TGG | GAC | TCC | CTG | TTT | TCT | GGC | TCC | CAG | GGT | CAA | GTG | CAA | CCC | 3600 |
| Pro | Ser | Trp | Asp | Ser | Leu | Phe | Ser | Gly | Ser | Gln | Gly | Gln | Val | Gln | Pro |  |
| 1185 |  |  |  |  | 1190 |  |  |  |  | 1195 |  |  |  |  | 1200 |
| GGG | GCC | CGC | ATC | TTT | TCT | TTT | GAC | GGC | AGA | GAT | GTC | CTG | AGA | CAC | CCA | 3648 |
| Gly | Ala | Arg | Ile | Phe | Ser | Phe | Asp | Gly | Arg | Asp | Val | Leu | Arg | His | Pro |  |

```
                        1205                         1210                         1215
GCC  TGG  CCG  CAG  AAG  AGC  GTA  TGG  CAC  GGC  TCG  GAC  CCC  AGT  GGG  CGG              3696
Ala  Trp  Pro  Gln  Lys  Ser  Val  Trp  His  Gly  Ser  Asp  Pro  Ser  Gly  Arg
               1220                    1225                         1230

AGG  CTG  ATG  GAG  AGT  TAC  TGT  GAG  ACA  TGG  CGA  ACT  GAA  ACT  ACT  GGG              3744
Arg  Leu  Met  Glu  Ser  Tyr  Cys  Glu  Thr  Trp  Arg  Thr  Glu  Thr  Thr  Gly
               1235                    1240                         1245

GCT  ACA  GGT  CAG  GCC  TCC  TCC  CTG  CTG  TCA  GGC  AGG  CTC  CTG  GAA  CAG              3792
Ala  Thr  Gly  Gln  Ala  Ser  Ser  Leu  Leu  Ser  Gly  Arg  Leu  Leu  Glu  Gln
               1250                    1255                         1260

AAA  GCT  GCG  AGC  TGC  CAC  AAC  AGC  TAC  ATC  GTC  CTG  TGC  ATT  GAG  AAT              3840
Lys  Ala  Ala  Ser  Cys  His  Asn  Ser  Tyr  Ile  Val  Leu  Cys  Ile  Glu  Asn
1265                    1270                         1275                    1280

AGC  TTC  ATG  ACC  TCT  TTC  TCC  AAA    TAGGCCTCTG  CCAGCTAGGG                            3884
Ser  Phe  Met  Thr  Ser  Phe  Ser  Lys
                         1285

TGGCAGACAG  AGGCCATGCA  GAACTTTGAC  ACAGCGCAGG  GAGCATTCAG  TCAGCACCCA                      3944

GGGCTCTGGC  TGGGATACAA  CTCCTGTATA  GTTCCCATTT  TTATGTAATC  CTCAAGAAAT                      4004

AAAAGGAAGC  CAAAGAGTAA  AAAAAAA                                                             4031
```

( 2 ) INFORMATION FOR SEQ ID NO: 2:

( i ) SEQUENCE CHARACTERISTICS:
        ( A ) LENGTH: 195
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 2:

```
Leu  Pro  Pro  Ala  Arg  Pro  Thr  Leu  Ser  Leu  Ala  His  Thr  His  Gln  Asp
 1                   5                        10                       15

Phe  Gln  Pro  Val  Leu  His  Leu  Val  Ala  Leu  Asn  Thr  Pro  Leu  Ser  Gly
                20                       25                  30

Gly  Met  Arg  Gly  Ile  Arg  Gly  Ala  Asp  Phe  Gln  Cys  Phe  Gln  Gln  Ala
               35                  40                       45

Arg  Ala  Val  Gly  Leu  Ser  Gly  Thr  Phe  Arg  Ala  Phe  Leu  Ser  Ser  Arg
     50                       55                       60

Leu  Gln  Asp  Leu  Tyr  Ser  Ile  Val  Arg  Arg  Ala  Asp  Arg  Gly  Ser  Val
 65                       70                  75                            80

Pro  Ile  Val  Asn  Leu  Lys  Asp  Glu  Val  Leu  Ser  Pro  Ser  Trp  Asp  Ser
                    85                       90                       95

Leu  Phe  Ser  Gly  Ser  Gln  Gly  Gln  Val  Gln  Pro  Gly  Ala  Arg  Ile  Phe
                    100                      105                 110

Ser  Phe  Asp  Gly  Arg  Asp  Val  Leu  Arg  His  Pro  Ala  Trp  Pro  Gln  Lys
               115                      120                      125

Ser  Val  Trp  His  Gly  Ser  Asp  Pro  Ser  Gly  Arg  Arg  Leu  Met  Glu  Ser
     130                      135                      140

Tyr  Cys  Glu  Thr  Trp  Arg  Thr  Glu  Thr  Thr  Gly  Ala  Thr  Gly  Gln  Ala
145                      150                      155                      160

Ser  Ser  Leu  Leu  Ser  Gly  Arg  Leu  Leu  Glu  Gln  Lys  Ala  Ala  Ser  Cys
                    165                      170                      175

His  Asn  Ser  Tyr  Ile  Val  Leu  Cys  Ile  Glu  Asn  Ser  Phe  Met  Thr  Ser
               180                      185                      190

Phe  Ser  Lys
          195
```

( 2 ) INFORMATION FOR SEQ ID NO: 3:

(i) SEQUENCE CHARACTERISTICS:
(A) LENGTH: 191
(B) TYPE: amino acid
(C) STRANDEDNESS: Not Relevant
(D) TOPOLOGY: Not Relevant (xi) SEQUENCE DESCRIPTION: SEQ ID NO: 3:

| Pro | His | Gln | Leu | Leu | Pro | Pro | Pro | Asn | Pro | Ile | Ser | Ser | Ala | Asn | Tyr |
|---|---|---|---|---|---|---|---|---|---|---|---|---|---|---|---|
| 1 | | | | 5 | | | | 10 | | | | | | 15 | |
| Glu | Lys | Pro | Ala | Leu | His | Leu | Ala | Ala | Leu | Asn | Met | Pro | Phe | Ser | Gly |
| | | | 20 | | | | 25 | | | | | 30 | | | |
| Asp | Ile | Arg | Ala | Asp | Phe | Gln | Cys | Phe | Lys | Gln | Ala | Arg | Ala | Ala | Gly |
| | | 35 | | | | 40 | | | | | 45 | | | | |
| Leu | Leu | Ser | Thr | Tyr | Arg | Ala | Pro | Leu | Ser | Ser | His | Leu | Gln | Asp | Leu |
| | 50 | | | | | 55 | | | | | 60 | | | | |
| Ser | Thr | Ile | Val | Arg | Lys | Ala | Glu | Arg | Tyr | Ser | Leu | Pro | Ile | Val | Asn |
| 65 | | | | | 70 | | | | 75 | | | | | | 80 |
| Leu | Lys | Gly | Gln | Val | Leu | Phe | Asn | Asn | Trp | Asp | Ser | Ile | Phe | Ser | Gly |
| | | | | 85 | | | | | 90 | | | | | 95 | |
| His | Gly | Gly | Gln | Pro | Asn | Met | His | Ile | Pro | Ile | Tyr | Ser | Phe | Asp | Gly |
| | | | | 100 | | | | 105 | | | | | | 110 | |
| Arg | Asp | Ile | Met | Thr | Asp | Pro | Ser | Trp | Pro | Gln | Lys | Val | Ile | Trp | His |
| | | | 115 | | | | 120 | | | | | 125 | | | |
| Gly | Ser | Ser | Pro | His | Gly | Val | Arg | Leu | Val | Asp | Asn | Tyr | Cys | Glu | Ala |
| | | 130 | | | | 135 | | | | | 140 | | | | |
| Trp | Arg | Thr | Ala | Asp | Thr | Ala | Val | Thr | Gly | Leu | Ala | Ser | Pro | Leu | Ser |
| 145 | | | | | 150 | | | | 155 | | | | | 160 | |
| Thr | Gly | Lys | Ile | Leu | Asp | Gln | Lys | Ala | Tyr | Ser | Cys | Ala | Asn | Arg | Leu |
| | | | | 165 | | | | | 170 | | | | | 175 | |
| Ile | Val | Leu | Cys | Ile | Glu | Asn | Ser | Phe | Met | Thr | Asp | Ala | Arg | Lys | |
| | | | 180 | | | | | 185 | | | | | 190 | | |

(2) INFORMATION FOR SEQ ID NO: 4:

(i) SEQUENCE CHARACTERISTICS:
(A) LENGTH: 3394
(B) TYPE: nucleic acid
(C) STRANDEDNESS: single
(D) TOPOLOGY: linear (xi) SEQUENCE DESCRIPTION: SEQ ID NO: 4:

| GGA | GAA | GTT | GGA | GCA | GAT | GGA | ATC | CCC | GGG | TTC | CCC | GGC | CTC | CCT | GGC | 48 |
|---|---|---|---|---|---|---|---|---|---|---|---|---|---|---|---|---|
| Gly | Glu | Val | Gly | Ala | Asp | Gly | Ile | Pro | Gly | Phe | Pro | Gly | Leu | Pro | Gly | |
| 1 | | | | 5 | | | | | 10 | | | | | 15 | | |
| AGA | GAG | GGC | ATT | GCT | GGG | CCC | CAG | GGG | CCA | AAG | GGA | GAC | AGA | GGC | AGC | 96 |
| Arg | Glu | Gly | Ile | Ala | Gly | Pro | Gln | Gly | Pro | Lys | Gly | Asp | Arg | Gly | Ser | |
| | | | 20 | | | | 25 | | | | | 30 | | | | |
| CGG | GGA | GAA | AAG | GGA | GAT | CCA | GGG | AAG | GAC | GGA | CTC | GGG | CAG | CCG | GGC | 144 |
| Arg | Gly | Glu | Lys | Gly | Asp | Pro | Gly | Lys | Asp | Gly | Leu | Gly | Gln | Pro | Gly | |
| | | 35 | | | | 40 | | | | | 45 | | | | | |
| CTC | CCT | GGC | CCC | CGC | GGA | CCC | CCG | GGA | CCT | GTG | GTC | TAC | GTG | TCG | GAG | 192 |
| Leu | Pro | Gly | Pro | Arg | Gly | Pro | Pro | Gly | Pro | Val | Val | Tyr | Val | Ser | Glu | |
| | 50 | | | | | 55 | | | | | 60 | | | | | |
| CAG | GAC | GGA | TCC | GTC | CTG | AGC | GTG | CCG | GGA | CCT | GAG | GGC | CGG | CGG | GGT | 240 |
| Gln | Asp | Gly | Ser | Val | Leu | Ser | Val | Pro | Gly | Pro | Glu | Gly | Arg | Arg | Gly | |
| 65 | | | | | 70 | | | | 75 | | | | | | 80 | |
| TTC | GCA | GGC | TTT | CCC | GGA | CCT | GCA | GGA | CCC | AAG | GGC | AAC | CTG | GGC | TCT | 288 |
| Phe | Ala | Gly | Phe | Pro | Gly | Pro | Ala | Gly | Pro | Lys | Gly | Asn | Leu | Gly | Ser | |
| | | | | 85 | | | | | 90 | | | | | 95 | | |

```
AAG GGC GAA CTA GGC TCC CCG GGA CCC AAG GGT GAG AAG GGT GAA CCG      336
Lys Gly Glu Leu Gly Ser Pro Gly Pro Lys Gly Glu Lys Gly Glu Pro
            100                 105                 110

GGC AGC ATC TTC AGC CCC GAC GGC GGT GCC CTG GGC CCT GCC CAG AAA      384
Gly Ser Ile Phe Ser Pro Asp Gly Gly Ala Leu Gly Pro Ala Gln Lys
            115                 120                 125

GGA GCC AAG GGA GAG CCG GGC TTC CGA GGA CCC CCG GGC CTA TAC GGA      432
Gly Ala Lys Gly Glu Pro Gly Phe Arg Gly Pro Pro Gly Leu Tyr Gly
130                 135                 140

CGG CCG GGG TAC AAG GGA GAG ATT GGC TTT CCT GGA CGG CCG GGT CGC      480
Arg Pro Gly Tyr Lys Gly Glu Ile Gly Phe Pro Gly Arg Pro Gly Arg
145                 150                 155                 160

CCC GGG ATG AAC GGA TTG AAA GGA GAG AAA GGG GAG CCG GGA GAT GCC      528
Pro Gly Met Asn Gly Leu Lys Gly Glu Lys Gly Glu Pro Gly Asp Ala
                165                 170                 175

AGC CTT GGA TTT GGC ATG AGG GGA ATG CCC GGC CCC CCA GGA CCT CCA      576
Ser Leu Gly Phe Gly Met Arg Gly Met Pro Gly Pro Pro Gly Pro Pro
            180                 185                 190

GGG CCC CCA GGC CCT CCA GGG ACT CCT GTT TAC GAC AGC AAT GTG TTT      624
Gly Pro Pro Gly Pro Pro Gly Thr Pro Val Tyr Asp Ser Asn Val Phe
        195                 200                 205

GCT GAG TCC AGC CGC CCC GGG CCT CCA GGA TTG CCA GGG AAT CAG GGC      672
Ala Glu Ser Ser Arg Pro Gly Pro Pro Gly Leu Pro Gly Asn Gln Gly
210                 215                 220

CCT CCA GGA CCC AAG GGC CCC AAA GGA GAA GTG GGC CCC CCC GGA CCA      720
Pro Pro Gly Pro Lys Gly Pro Lys Gly Glu Val Gly Pro Pro Gly Pro
225                 230                 235                 240

CCA GGG CAG TTT CCG TTT GAC TTT CTT CAG AAG GAG GCT GAA ATG AAG      768
Pro Gly Gln Phe Pro Phe Asp Phe Leu Gln Lys Glu Ala Glu Met Lys
            245                 250                 255

GGG GAG AAG GGA GAC CGA GGT GAT GCA GGA CAG AAA GGC GAA AGG GGG      816
Gly Glu Lys Gly Asp Arg Gly Asp Ala Gly Gln Lys Gly Glu Arg Gly
            260                 265                 270

GAG CCC GGG GGC GGC GGT TTC TTC GGC TCC AGC CTG CCC GGG GCC CCC      864
Glu Pro Gly Gly Gly Gly Phe Phe Gly Ser Ser Leu Pro Gly Ala Pro
        275                 280                 285

GGC GCC CCA GGC CCA CGT GGC TAC CCT GGG ATT CCA GGT CCC AAG GGA      912
Gly Ala Pro Gly Pro Arg Gly Tyr Pro Gly Ile Pro Gly Pro Lys Gly
        290                 295                 300

GAG AGC ATC CGG GGC CAG CCC GGC CCA CCT GGA CCT CAG GGA CCC CCC      960
Glu Ser Ile Arg Gly Gln Pro Gly Pro Pro Gly Pro Gln Gly Pro Pro
305                 310                 315                 320

GGC ATC GGC TAC GAG GGG CGC CAG GGC CCT CCC GGC CCC CCA GGC CCC     1008
Gly Ile Gly Tyr Glu Gly Arg Gln Gly Pro Pro Gly Pro Pro Gly Pro
                325                 330                 335

CCA GGG CCC CCT TCA TTT CCT GGC CCT CAC AGG CAG ACT ATC AGC GTT     1056
Pro Gly Pro Pro Ser Phe Pro Gly Pro His Arg Gln Thr Ile Ser Val
            340                 345                 350

CCG GGG CCT CCG GGC CCC CCT GGG CCC CCT GGG CCC CCT GGA ACC ATG     1104
Pro Gly Pro Pro Gly Pro Pro Gly Pro Pro Gly Pro Pro Gly Thr Met
            355                 360                 365

GGC GCC TCC TCA GGG CAG GTG AGG CTC TGG GCT ACA CGC CAG GCC ATG     1152
Gly Ala Ser Ser Gly Gln Val Arg Leu Trp Ala Thr Arg Gln Ala Met
370                 375                 380

CTG GGC CAG GTG CAC GAG GTT CCC GAG GGC TGG CTC ATC TTC GTG GCC     1200
Leu Gly Gln Val His Glu Val Pro Glu Gly Trp Leu Ile Phe Val Ala
385                 390                 395                 400

GAG CAG GAG GAG CTC TAC GTC CGC GTG CAG AAC GGG TTC CGG AAG GTC     1248
Glu Gln Glu Glu Leu Tyr Val Arg Val Gln Asn Gly Phe Arg Lys Val
                405                 410                 415
```

-continued

| | | | | | | | | | | | | | | | | |
|---|---|---|---|---|---|---|---|---|---|---|---|---|---|---|---|---|
| CAG | CTG | GAG | GCC | CGG | ACA | CCA | CTC | CCA | CGA | GGG | ACG | GAC | AAT | GAA | GTG | 1296 |
| Gln | Leu | Glu | Ala<br>420 | Arg | Thr | Pro | Leu | Pro<br>425 | Arg | Gly | Thr | Asp | Asn<br>430 | Glu | Val | |
| GCC | GCC | TTG | CAG | CCC | CCC | GTG | GTG | CAG | CTG | CAC | GAC | AGC | AAC | CCC | TAC | 1344 |
| Ala | Ala | Leu<br>435 | Gln | Pro | Pro | Val | Val<br>440 | Gln | Leu | His | Asp | Ser<br>445 | Asn | Pro | Tyr | |
| CCG | CGG | CGG | GAG | CAC | CCC | CAC | CCC | ACC | GCG | CGG | CCC | TGG | CGG | GCA | GAT | 1392 |
| Pro | Arg<br>450 | Arg | Glu | His | Pro | His<br>455 | Pro | Thr | Ala | Arg | Pro<br>460 | Trp | Arg | Ala | Asp | |
| GAC | ATC | CTG | GCC | AGC | CCC | CCT | GGG | CTG | CCC | GAG | CCC | CAG | CCC | TAC | CCC | 1440 |
| Asp<br>465 | Ile | Leu | Ala | Ser | Pro<br>470 | Pro | Gly | Leu | Pro | Glu<br>475 | Pro | Gln | Pro | Tyr | Pro<br>480 | |
| GGA | GGC | CCG | CAC | CAC | AGC | TCC | TAC | GTG | CAC | TGC | GGC | CCG | GCA | CGA | CCC | 1488 |
| Gly | Gly | Pro | His | His<br>485 | Ser | Ser | Tyr | Val | His<br>490 | Cys | Gly | Pro | Ala | Arg<br>495 | Pro | |
| ACA | AGC | CCA | CCC | GCC | CAC | AGC | CAC | CGC | GAC | TTC | CAG | CCG | GTG | CTC | CAC | 1536 |
| Thr | Ser | Pro<br>500 | Pro | Ala | His | Ser | His<br>505 | Arg | Asp | Phe | Gln | Pro<br>510 | Val | Leu | His | |
| CTG | GTT | GCG | CTC | AAC | AGC | CCC | CTG | TCA | GGC | GGC | ATG | CGG | GGC | ATC | CGC | 1584 |
| Leu | Val | Ala<br>515 | Leu | Asn | Ser | Pro | Leu<br>520 | Ser | Gly | Gly | Met | Arg<br>525 | Gly | Ile | Arg | |
| GGG | GCC | GAC | TTC | CAG | TGC | TTC | CAG | CAG | GCG | CGG | GCC | GTG | GGG | CTG | GCG | 1632 |
| Gly | Ala | Asp<br>530 | Phe | Gln | Cys | Phe<br>535 | Gln | Gln | Ala | Arg | Ala<br>540 | Val | Gly | Leu | Ala | |
| GGC | ACC | TTC | CGC | GCC | TTC | CTG | TCC | TCG | CGC | CTG | CAG | GAC | CTG | TAC | AGC | 1680 |
| Gly<br>545 | Thr | Phe | Arg | Ala | Phe<br>550 | Leu | Ser | Ser | Arg | Leu<br>555 | Gln | Asp | Leu | Tyr | Ser<br>560 | |
| ATC | GTG | CGC | CGT | GCC | GAC | CGC | GCA | GCC | GTG | CCC | ATC | GTC | AAC | CTC | AAG | 1728 |
| Ile | Val | Arg | Arg | Ala<br>565 | Asp | Arg | Ala | Ala | Val<br>570 | Pro | Ile | Val | Asn | Leu<br>575 | Lys | |
| GAC | GAG | CTG | CTG | TTT | CCC | AGC | TGG | GAG | GCT | CTG | TTC | TCA | GGC | TCT | GAG | 1776 |
| Asp | Glu | Leu | Leu<br>580 | Phe | Pro | Ser | Trp | Glu<br>585 | Ala | Leu | Phe | Ser | Gly<br>590 | Ser | Glu | |
| GGT | CCG | CTG | AAG | CCC | GGG | GCA | CGC | ATC | TTC | TCC | TTT | GAC | GGC | AAG | GAC | 1824 |
| Gly | Pro | Leu<br>595 | Lys | Pro | Gly | Ala | Arg<br>600 | Ile | Phe | Ser | Phe | Asp<br>605 | Gly | Lys | Asp | |
| GTC | CTG | AGG | CAC | CCC | ACC | TGG | CCC | CAG | AAG | AGC | GTG | TGG | CAT | GGC | TCG | 1872 |
| Val | Leu<br>610 | Arg | His | Pro | Thr | Trp<br>615 | Pro | Gln | Lys | Ser | Val<br>620 | Trp | His | Gly | Ser | |
| GAC | CCC | AAC | GGG | CGC | AGG | CTG | ACC | GAG | AGC | TAC | TGT | GAG | ACG | TGG | CGG | 1920 |
| Asp<br>625 | Pro | Asn | Gly | Arg | Arg<br>630 | Leu | Thr | Glu | Ser | Tyr<br>635 | Cys | Glu | Thr | Trp | Arg<br>640 | |
| ACG | GAG | GCT | CCC | TCG | GCC | ACG | GGC | CAG | GCC | TCC | TCG | CTG | CTG | GGG | GGC | 1968 |
| Thr | Glu | Ala | Pro | Ser<br>645 | Ala | Thr | Gly | Gln | Ala<br>650 | Ser | Ser | Leu | Leu | Gly<br>655 | Gly | |
| AGG | CTC | CTG | GGG | CAG | AGT | GCC | GCG | AGC | TGC | CAT | CAC | GCC | TAC | ATC | GTG | 2016 |
| Arg | Leu | Leu | Gly<br>660 | Gln | Ser | Ala | Ala | Ser<br>665 | Cys | His | His | Ala | Tyr<br>670 | Ile | Val | |
| CTC | TGC | ATT | GAG | AAC | AGC | TTC | ATG | ACT | GCC | TCC | AAG | | | | | 2052 |
| Leu | Cys | Ile<br>675 | Glu | Asn | Ser | Phe | Met<br>680 | Thr | Ala | Ser | Lys | | | | | |

TAGCCACCGC CTGGATGCAG ATGGCCGGAG AGGACCGGCG GCTCGGAGGA AGCCCCCACC   2112

GTGGGCAGGG AGCAGCCGGC CAGCCCCTGG CCCCAGGACC TGGCTGCCAT ACTTTCCTGT   2172

ATAGTTCACG TTTCATGTAA TCCTCAAGAA ATAAAAGGAA GCCAAAGAGT GTATTTTTT    2232

AAAAGTTTAA AACAGAAGCC TGATGCTGAC ATTCACCTGC CCCAACTCTC CCCTGACCTG   2292

TGAGCCCAGC TGGGTCAGGC AGGGTGCAGT ATCATGCCCT GTGCAACCTC TTGGCCTGAT   2352

CAGACCACGG CTCGATTTCT CCAGGATTTC CTGCTTTGGG AAACCGTGCT CGCCCCAGCA   2412

| | | | | | |
|---|---|---|---|---|---|
| GGTGCTGACT | TCATCTCCCA | CCTAGCAGCA | CCGTTCTGTG | CACAAAACCC | AGACCTGTTA | 2472
| GCAGACAGGC | CCCGTGAGGC | AATGGGAGCT | GAGGCCACAC | TCAGCACAAG | GCCATCTGGG | 2532
| CTCCTCCAGG | GTGTGTGCTC | GCCCTGCGGT | AGATGGGAGG | GAGGCTCAGG | TCCCTGGGGC | 2592
| TAGGGGGAGC | CCCTTCTGCT | CAGCTCTGGG | CCATTCTCCA | CAGCAACCCC | AGGCTGAAGC | 2652
| AGGTTCCCAA | GCTCAGAGGC | GCACTGTGAC | CCCCAGCTCC | GGCCTGTCCT | CCAACACCAA | 2712
| GCACAGCAGC | CTGGGGCTGG | CCTCCCAAAT | GAGCCATGAG | ATGATACATC | CAAAGCAGAC | 2772
| AGCTCCACCC | TGGCCGAGTC | CAAGCTGGGA | GATTCAAGGG | ACCCATGAGT | TGGGGTCTGG | 2832
| CAGCCTCCCA | TCCAGGGCCC | CCATCTCATG | CCCCTGGCTG | GGACGTGCTC | AGCCAGCACT | 2892
| TGTCCAGCTG | AGCGCCAGGA | TGGAACACGG | CCACATCAAA | GAGGCTGAGG | CTGGCACAGG | 2952
| ACATGCGGTA | GCCAGCACAC | AGGGCAGTGA | GGGAGGGCTG | TCATCTGTGC | ACTGCCCATG | 3012
| GACAGGCTGG | CTCCAGATGC | AGGGCAGTCA | TTGGCTGTCT | CCTAGGAAAC | CCATATCCTT | 3072
| ACCCTCCTTG | GGACTGAAGG | GGAACCCCGG | GGTGCCCACA | GGCCGCCCTG | CGGGTGAACA | 3132
| AAGCAGCCAC | GAGGTGCAAC | AAGGTCCTCT | GTCAGTCACA | GCCACCCCTG | AGATCCGGCA | 3192
| ACATCAACCC | CAGAGTCATT | CGTTCTGTGG | AGGGACAAGT | GGACTCAGGG | CAGCGCCAGG | 3252
| CTGACCACAG | CACAGCCAAC | ACGCACCTGC | CTCAGGACTG | CGACGAAACC | GGTGGGGCTG | 3312
| GTTCTGTAAT | TGTGTGTGAT | GTGAAGCCAA | TTCAGACAGG | CAAATAAAAG | TGACCTTTTA | 3372
| CACTGAAAAA | AAAAAAAAAA | AA | | | | 3394

( 2 ) INFORMATION FOR SEQ ID NO: 5:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( x i ) SEQUENCE DESCRIPTION: SEQ ID NO: 5:

TGTGTGACTT GCTGCTTT                                                                    18

( 2 ) INFORMATION FOR SEQ ID NO: 6:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( x i ) SEQUENCE DESCRIPTION: SEQ ID NO: 6:

TAGCTCCAGT CCCTGCGA                                                                    18

( 2 ) INFORMATION FOR SEQ ID NO: 7:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( x i ) SEQUENCE DESCRIPTION: SEQ ID NO: 7:

CCGAGCAAAT GGCACCCT                                                                    18

( 2 ) INFORMATION FOR SEQ ID NO: 8:

( i ) SEQUENCE CHARACTERISTICS:
    ( A ) LENGTH: 18
    ( B ) TYPE: nucleic acid
    ( C ) STRANDEDNESS: single ( D ) TOPOLOGY: linear ( x i ) SEQUENCE DESCRIPTION: SEQ ID NO: 8:

CATACTTCC TGTATACT                                                                                                            18

( 2 ) INFORMATION FOR SEQ ID NO: 9:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 9:

CCTCAGCCAC TTTGATGT                                                                                                            18

We claim:

1. An isolated nucleic acid encoding a polypeptide having 95% identity to the human α1 (XVIII) collagen encoded by the nucleic acid sequence of SEQ ID NO:4, said polypeptide comprising the sequence Gly-X-Y-Gly-X'-Y', where X, Y, X', and Y' represent any amino acid.

2. The nucleic acid of claim 1, said nucleic acid encoding human α1 (XVIII) collagen encoded by the nucleic acid sequence of SEQ ID NO:4.

3. A plasmid comprising the nucleic acid of claim 1.

4. The plasmid of claim 3, said plasmid further comprising an expression control sequence capable of directing expression of said α1 (XVIII) collagen polypeptide.

5. A host cell comprising the nucleic acid of claim 1.

6. The host cell of claim 5 wherein said cell is a prokaryotic cell.

7. The cell of claim 5 wherein said cell is a eukaryotic cell.

8. The cell of claim 7 wherein said cell is mammalian cell.

\* \* \* \* \*

UNITED STATES PATENT AND TRADEMARK OFFICE
CERTIFICATE OF CORRECTION

PATENT NO. : 5,643,783

DATED : July 1, 1997

INVENTOR(S) : Bjorn R. Olsen and Suk P. Oh

It is certified that error appears in the above-identified patent and that said Letters Patent is hereby corrected as shown below:

In column 1, before "Background of the Invention" insert the following paragraph:

--This invention was supported by NIH grants AR 36819, AR 36820, and HL 33014, and the government has certain rights to the invention.--

Signed and Sealed this

Tenth Day of March, 1998

Attest:

BRUCE LEHMAN

Attesting Officer

Commissioner of Patents and Trademarks